United States Patent
Kitano et al.

(10) Patent No.: US 10,361,647 B2
(45) Date of Patent: Jul. 23, 2019

(54) MOTOR DRIVE CONTROLLING APPARATUS, MOTOR DRIVE CONTROLLING METHOD, AND TUBE PUMP

(71) Applicant: MINEBEA MITSUMI Inc., Nagano (JP)

(72) Inventors: Takamichi Kitano, Shizuoka (JP); Hidetoshi Hijikata, Shizuoka (JP)

(73) Assignee: MINEBEA MITSUMI INC., Nagano (JP)

( * ) Notice: Subject to any disclaimer, the term of this patent is extended or adjusted under 35 U.S.C. 154(b) by 0 days.

(21) Appl. No.: 15/942,620

(22) Filed: Apr. 2, 2018

(65) Prior Publication Data
US 2018/0287528 A1 Oct. 4, 2018

(30) Foreign Application Priority Data
Apr. 3, 2017 (JP) .................... 2017-073557

(51) Int. Cl.
*G05B 11/01* (2006.01)
*H02P 6/24* (2006.01)
(Continued)

(52) U.S. Cl.
CPC ............ *H02P 6/24* (2013.01); *A61M 1/1039* (2014.02); *A61M 1/1046* (2013.01); *A61M 1/1086* (2013.01); *A61M 1/14* (2013.01); *F04B 43/1253* (2013.01); *F04B 49/02* (2013.01); *F04B 49/20* (2013.01); *F04B 51/00* (2013.01); *H02P 6/085* (2013.01); *H02P 6/16* (2013.01);
(Continued)

(58) Field of Classification Search
CPC ...... H02P 6/24; H02P 29/0241; A61M 1/1039
USPC ......................................... 318/628
See application file for complete search history.

(56) References Cited

U.S. PATENT DOCUMENTS 7,633,256 B2* 12/2009 Reichert ............. G02B 26/122
  318/602
9,328,727 B2* 5/2016 Koehl ................ F04D 15/0088
(Continued)

FOREIGN PATENT DOCUMENTS

JP   10-290831 A   11/1998

OTHER PUBLICATIONS

Extended European Search Report for corresponding European Application No. 18165021.9 dated Aug. 22, 2018.

*Primary Examiner* — Erick D Glass
(74) *Attorney, Agent, or Firm* — Pearne & Gordon LLP

(57) ABSTRACT

A motor drive controlling apparatus includes: a controller that generates and outputs a drive control signal, in response to input of a speed command signal and a rotational direction signal; a motor driver that generates and outputs a drive signal to a motor, in response to the drive control signal; and an encoder that detects a rotational position of the motor to output an encoder signal. The controller includes: a measurement unit that detects, based on the encoder signal, a time at which a rotational state of the motor becomes, caused by an external factor, different from that commanded by the speed command and rotational direction signals, and measures a movement amount from the time; and a transmitting unit that transmits, to the motor driver, a signal for stopping an output of the drive signal, when the movement amount and a drive-control-signal outputting state satisfy a predetermined condition.

11 Claims, 15 Drawing Sheets

(51) Int. Cl.
   *H02P 6/16*     (2016.01)
   *A61M 1/10*    (2006.01)
   *A61M 1/14*    (2006.01)
   *F04B 49/20*   (2006.01)
   *F04B 51/00*   (2006.01)
   *F04B 49/02*   (2006.01)
   *F04B 43/12*   (2006.01)
   *H02P 6/08*    (2016.01)
   *H02P 29/024*  (2016.01)

(52) U.S. Cl.
   CPC . *H02P 29/0241* (2016.02); *A61M 2205/3317* (2013.01); *A61M 2205/3327* (2013.01); *A61M 2205/3365* (2013.01)

(56) References Cited

U.S. PATENT DOCUMENTS

| | | | |
|---|---|---|---|
| 9,567,992 B2* | 2/2017 | Heide | F04B 43/12 |
| 2007/0108930 A1 | 5/2007 | Yokouchi et al. | |
| 2012/0323157 A1 | 12/2012 | O'Mahony et al. | |
| 2013/0280104 A1* | 10/2013 | Heide | F04B 43/12 417/53 |

* cited by examiner ered rotational state based on a combination of the speed command signal and the rotational direction signal, and measures a movement amount from a rotational position at the time point at which the rotational state of the motor becomes the different state. The transmitting unit transmits, to the motor driver, a stop control signal for stopping an output of the drive signal, when the movement amount and an outputting state of the drive control signal satisfy a predetermined condition.
MOTOR DRIVE CONTROLLING APPARATUS, MOTOR DRIVE CONTROLLING METHOD, AND TUBE PUMP

CROSS-REFERENCE TO RELATED APPLICATION

The present application claims priority to and incorporates by reference the entire contents of Japanese Patent Application No. 2017-073557 filed in Japan on Apr. 3, 2017.

BACKGROUND OF THE INVENTION

1. Field of the Invention

The present invention relates to a motor drive controlling apparatus, a motor drive controlling method, and a tube pump.

2. Description of the Related Art

Conventionally, there has been known a tube pump of related art as a pump apparatus. The tube pump delivers liquid contained in a tube by causing a motor to rotate rollers while pressing and flattening the tube. The tube pump is used in a medical apparatus, and there has been known a pump apparatus (blood pump) for artificial dialysis in which a brushless direct current (DC) motor rotates a rotor having rollers, for example.

There exist, for example, a 120-degree conduction method and a 180-degree conduction method among conduction methods of this brushless DC motor used in the tube pump. Commonly, this brushless DC motor to be operated in the 180-degree conduction method starts to rotate in the 120-degree conduction method, and switches to the low-noise and low-vibration 180-degree conduction method in accordance with an actual rotational speed of the motor. When an external factor causes the actual rotational speed of the motor to fall below a predetermined rotational speed, the conduction method is switched from the 180-degree conduction method to the 120-degree conduction method so as to sustain the control over the motor (see Japanese Laid-open Patent Publication No. 10-290831).

However, when a motor moves from a target rotational position due to an external factor before a conduction method has switched from the 180-degree conduction method to the 120-degree conduction method, a brushless DC motor used in a conventional tube pump is in a protective operation (for example, short brake) until the motor has been stopped. In a state where a reverse speed of the motor becomes extremely low, which is regarded that the motor is stopped, or "0" to release the protective operation, the motor is rapidly accelerated in order to return the motor to the target rotational position and thus flow volume per unit time instantaneously increases, furthermore, when the pump is in a heavy load state during this rapid acceleration, there exists possibility that a rapid pressure rise causes a breakage in a tube.

SUMMARY OF THE INVENTION

A motor drive controlling apparatus includes a controller, a motor driver, and a position detector. The controller generates and outputs a drive control signal, in response to an input of a speed command signal and a rotational direction signal. The motor driver generates a drive signal and outputs the generated drive signal to a motor, in response to an input of the drive control signal. The position detector detects a rotational position of the motor and outputs a detection signal that is based on a detection result. The controller includes a measurement unit and a transmitting unit. The measurement unit detects, on the basis of the detection signal, a time point at which a rotational state of the motor becomes, caused by an external factor, a different state that is different from a commanded rotational state based on a combination of the speed command signal and the rotational direction signal, and measures a movement amount from a rotational position at the time point at which the rotational state of the motor becomes the different state. The transmitting unit transmits, to the motor driver, a stop control signal for stopping an output of the drive signal, when the movement amount and an outputting state of the drive control signal satisfy a predetermined condition.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENT

Figure 1:
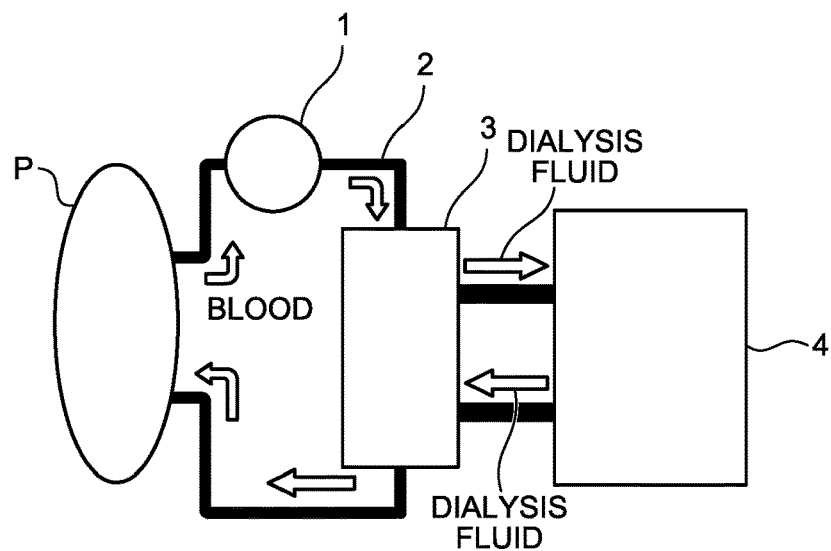
FIG. 1 is a diagram illustrating a configuration example of a dialysis system into which a blood pump according to an embodiment is assembled.

Hereinafter, a motor drive controlling apparatus, a motor drive controlling method, and a tube pump according to an embodiment will be explained with reference to accompanying drawings. Relations between numeric values of elements and ratios between the elements among other things that are illustrated in the drawings are merely one example, and may be different from those of reality. A part or all of the numeric values and the ratios illustrated in one of the accompanying drawings may be different from those illustrated in another.

Embodiment

Hereinafter, a case will be explained in which a tube pump to be controlled by a motor drive controlling apparatus according to the embodiment is a blood pump of a dialysis system. FIG. 1 is a diagram illustrating a configuration example of the dialysis system into which the blood pump according to the embodiment is assembled.

The dialysis system illustrated in FIG. 1 includes a blood pump 1 (one example of tube pump), a dialyzer 3, and a dialysis fluid supplier 4. The blood pump 1 transports the blood of a patient P to the dialyzer 3 via tubes 2 (namely, "blood removal").

This dialyzer 3 performs, on the blood of the patient P, processes for removing wastes, maintaining electrolytes, and maintaining water amount, by using semipermeable membranes and dialysis fluid that is supplied from the dialysis fluid supplier 4. The blood pump 1 returns the blood that has been processed by the dialyzer 3 to the patient P via the tubes 2 (namely, "blood return").

Figure 2:
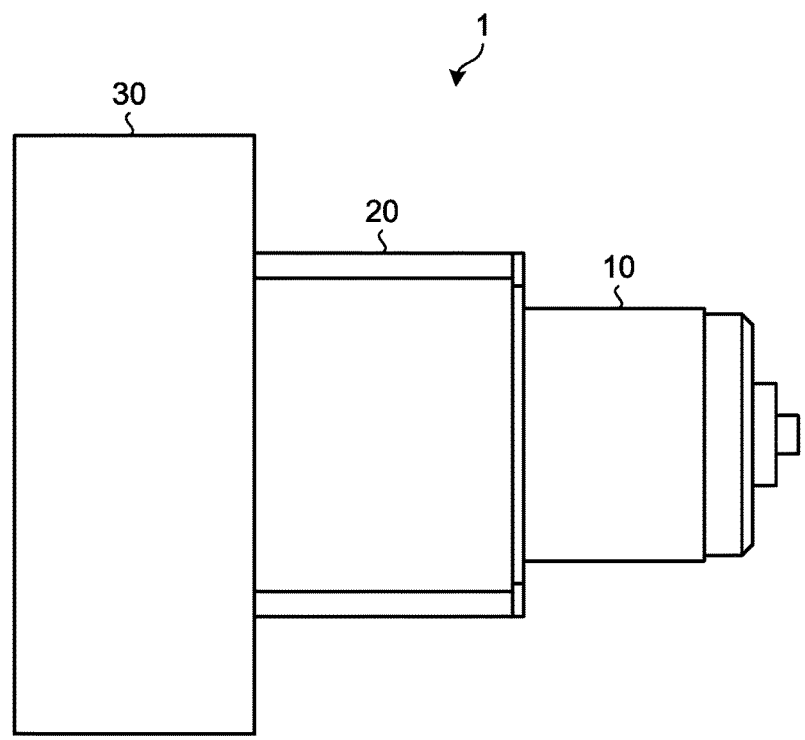
FIG. 2 is a first diagram illustrating the blood pump illustrated in FIG. 1.
Figure 3:
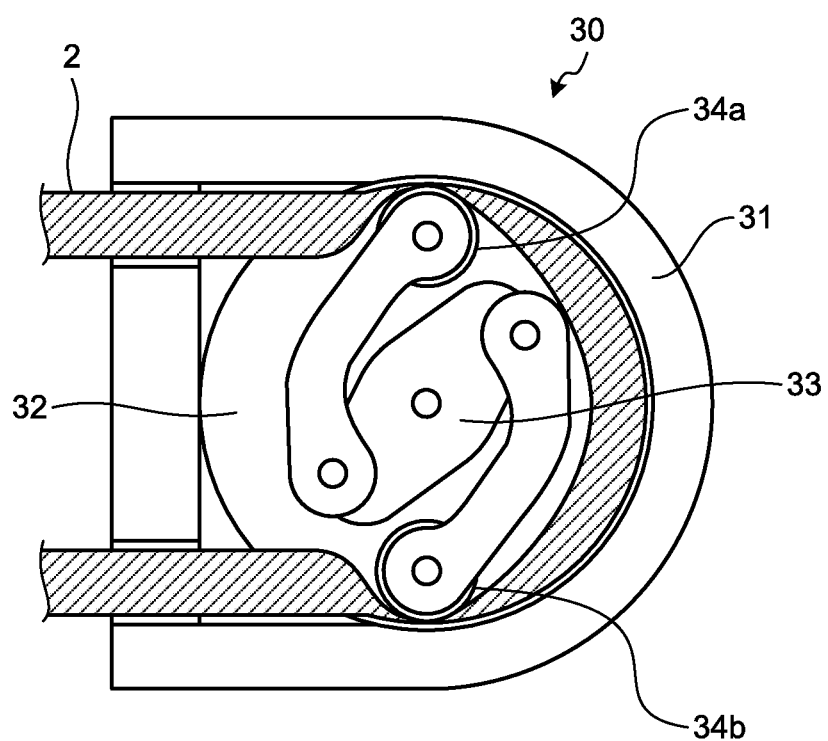
FIG. 3 is a second diagram illustrating the blood pump illustrated in FIG. 1.

FIGS. 2 and 3 are diagrams illustrating the blood pump 1 illustrated in FIG. 1. As illustrated in FIG. 2, the blood pump 1 includes a motor apparatus 10, a speed reducer 20, and a pump system 30. FIG. 2 is a side view illustrating the blood pump 1 illustrated in FIG. 1, and FIG. 3 is a diagram illustrating the blood pump 1 illustrated in FIG. 1 as viewed from a side facing the pump system 30.

In FIG. 2, the motor apparatus 10 is a drive source that supplies rotational drive force to a rotor 32 (see FIG. 3) of the pump system 30 via the speed reducer 20, and has a motor 11 (see FIG. 7) to be mentioned later that is built therein. The speed reducer 20 is connected with a rotating shaft of the motor apparatus 10 (motor 11) so as to reduce a rotational speed of the motor 11 in accordance with a predetermined reduction ratio. The pump system 30 is connected with a rotating shaft (output shaft) of the speed reducer 20.

As illustrated in FIG. 3, the pump system 30 includes a housing 31, the rotor 32, a roller support 33, a roller 34a, and a roller 34b. The housing 31 is provided therein with an internal space for accommodating the tube 2 and the rotor 32. The tube 2 is disposed along an arc-shaped inner circumferential wall surface of the housing 31. The rotor 32 is connected with the rotating shaft (output shaft) of the speed reducer 20.

The roller support 33 is connected with the rotor 32, and is rotated together with the rotation of the rotor 32. The roller 34a and the roller 34b are attached to opposite ends of the roller support 33. The roller support 33 supports the roller 34a and the roller 34b, which depress the tube 2, to be rotatable.

The roller 34a and the roller 34b are rotated together with the rotation of the roller support 33. In other words, the roller 34a and the roller 34b rotate when driven by the motor apparatus 10 (motor 11), and depress the tube 2 disposed along the inner circumferential wall surface of the housing 31 so as to deliver the liquid (blood) contained in the tube 2.

Figure 4:
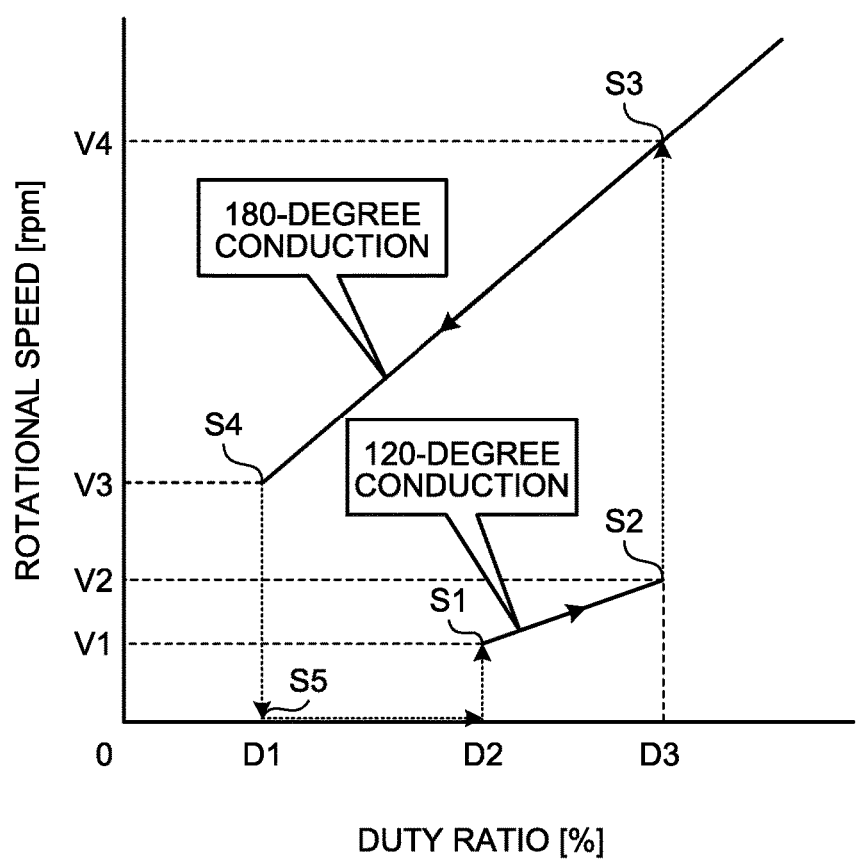
FIG. 4 is a diagram illustrating one example of a switching operation between conduction methods to be performed by a motor apparatus according to the embodiment.

FIG. 4 is a diagram illustrating one example of a switching operation between conduction methods to be performed by the motor apparatus 10 according to the embodiment. As illustrated in FIG. 4, the conduction methods of the motor 11 of the motor apparatus 10 have a 120-degree conduction method (hereinafter, may be referred to as "120-degree conduction") and a 180-degree conduction method (hereinafter, may be referred to as "180-degree conduction").

The 120-degree conduction is a conduction method to be used when the motor 11 is driven at a low rotational speed (for example, V1 to V2 rpm). The 180-degree conduction is a conduction method to be used when the motor 11 is driven at a middle to high rotational speed (for example, V3 rpm or more). In the following embodiment, a case will be explained as one example in which V1 to V2 rpm is smaller than 100 rpm, V3 rpm is larger than 100 rpm, and V4 rpm is larger than V3 rpm.

The 120-degree conduction has an advantage that a torque at a low rotational speed is large, on the contrary, has a disadvantage that driving noise and vibration are large at a middle to high rotational speed. On the other hand, the 180-degree conduction has a disadvantage that a torque at the low rotational speed is smaller than that of the 120-degree conduction, on the contrary, has an advantage that driving noise and vibration are small at the middle to high rotational speed.

Hence, in the present embodiment, a control is performed in which a current is supplied under the 120-degree conduction at a start-up of the motor 11 and the 120-degree conduction is switched into the 180-degree conduction when an actual rotational speed is a predetermined rotational speed (for example, V2 rpm) or more.

In the example illustrated in FIG. 4, when the motor 11 is rotated at a low rotational speed (for example, 100 rpm), the following control is performed. First, when a pulse width modulation (PWM) duty ratio (hereinafter, may be referred to as "duty ratio") of the motor 11 is increased by the 120-degree conduction, the motor 11 starts to rotate at D2%, and the rotational speed becomes V1 rpm (Step S1).

Subsequently, when the duty ratio is increased and the rotational speed is V2 rpm or more at D3% (Step S2), the conduction method is switched into the 180-degree conduction from the 120-degree conduction (Step S3). The rotational speed of the motor 11 rapidly increases from V2 rpm to V4 rpm to exceed a target rotational speed (100 rpm).

Next, when the duty ratio is reduced while maintaining the 180-degree conduction, the rotational speed is V3 rpm at D1% (Step S4). Subsequently, when the duty ratio is reduced, the rotational speed is reduced in a free state where the motor 11 is not able to rotate due to insufficient torque, and the conduction method is switched into the 120-degree conduction from the 180-degree conduction when the rotational speed is V2 rpm or less (Step S5).

The duty is increased when the rotational speed is 100 rpm or less, however, the free state continues in which the motor 11 is not able to rotate (Steps S4 to S5 and Steps S5 to S1), and the motor 11 restarts to rotate under the 120-degree conduction at D2% (Step S1). In this manner, the motor 11 repeats the steps of the 120-degree conduction (Steps S1 to S2), the 180-degree conduction (Steps S3 to S4), and the free (Steps S4 to S5 and Steps S5 to S1), so that it is possible to cause an average value of the rotational speed of the motor 11 to be the target rotational speed (100 rpm).

As described above, in the present embodiment, the motor 11 is used while being decelerated by the speed reducer 20, even when the rotational speed microscopically fluctuates due to repetition of the above-mentioned steps, there exists no problem in practical use.

Figure 5:
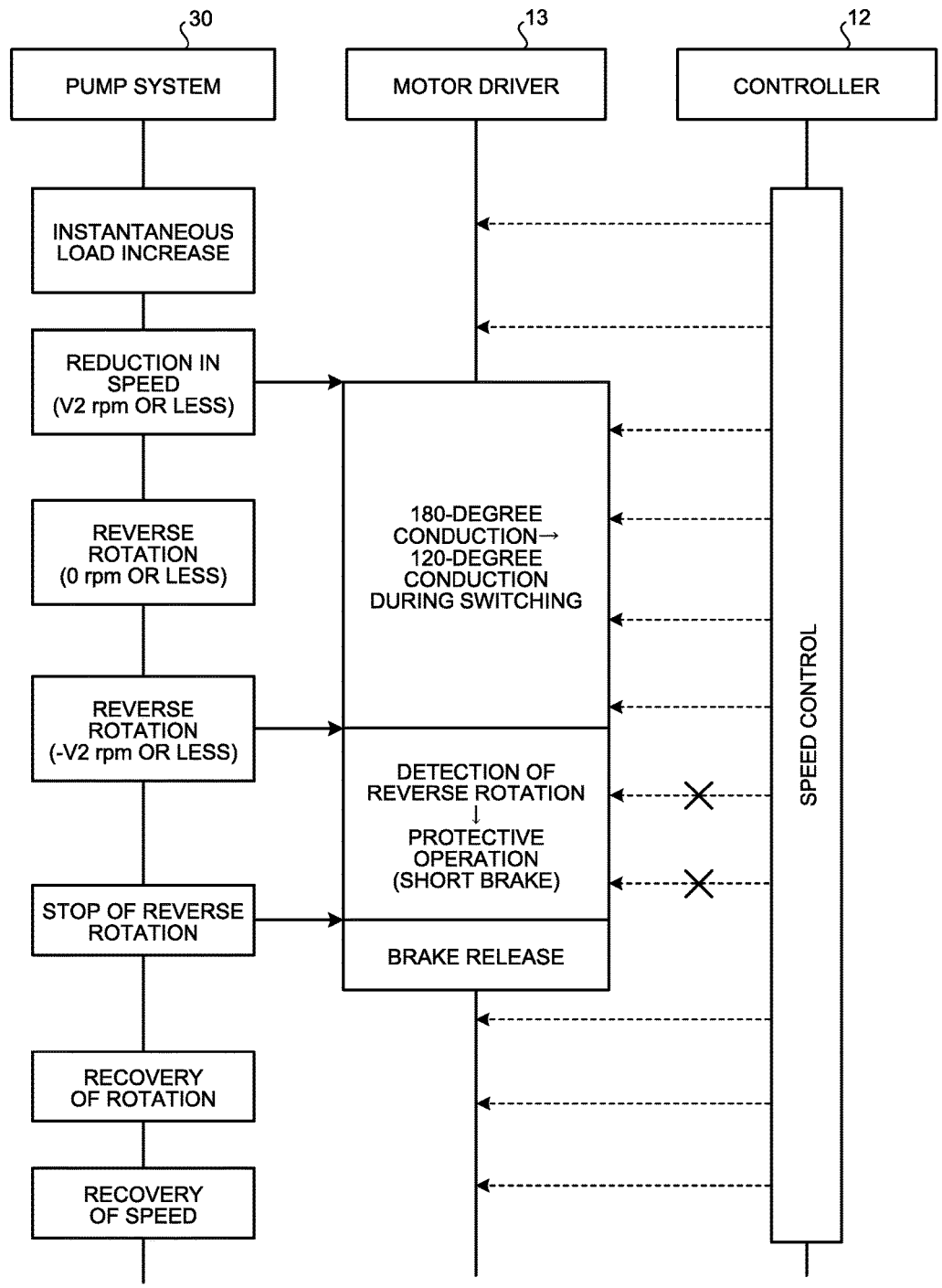
FIG. 5 is a diagram illustrating a processing procedure to be executed by a motor drive controlling apparatus according to a reference example.
Figure 6:
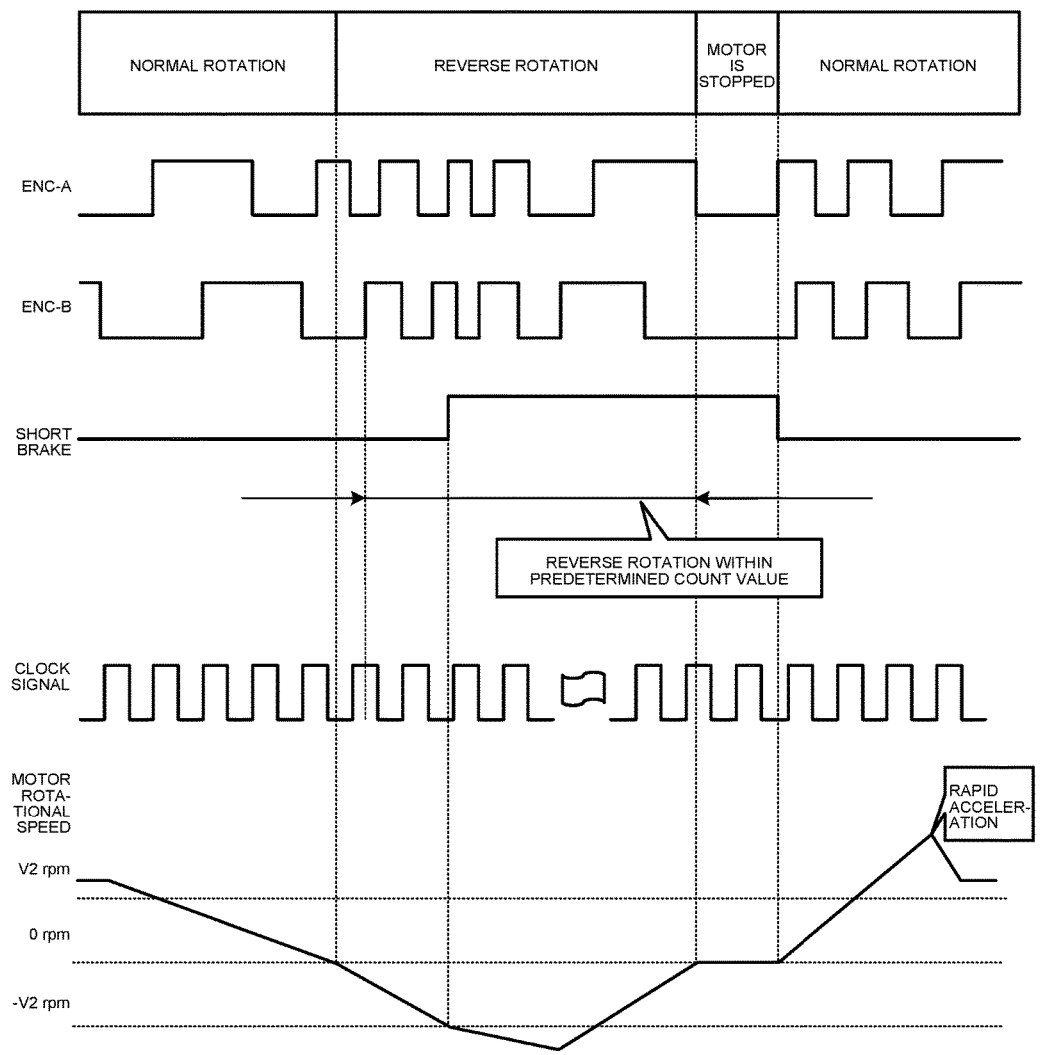
FIG. 6 is a timing diagram illustrating one example of a relation between signal elements of the motor drive controlling apparatus according to the reference example.

Next, a problem of this motor apparatus 10 will be explained with reference to FIGS. 5 and 6. FIG. 5 is a diagram illustrating a processing procedure to be executed by a motor drive controlling apparatus according to a reference example. FIG. 6 is a timing diagram illustrating one example of a relation between signal elements of the motor drive controlling apparatus according to the reference example.

As illustrated in FIG. 5, a motor driver 13 (see FIG. 7) outputs a drive signal to the motor 11 (see FIG. 7) so as to drive the motor 11. This drive signal is generated in the motor driver 13 on the basis of the 120-degree conduction method or the 180-degree conduction method to be output to the motor 11.

A controller 12 (see FIG. 7) outputs a drive control signal to the motor driver 13 so as to perform various controls on the motor driver 13. For example, the controller 12 transmits a speed command to the motor driver 13 on the basis of a speed command signal given by a user and an encoder signal (see FIG. 7) output from an encoder 14, so as to control the rotational speed of the motor 11 (speed control).

Here, when a load on the pump system 30 during the low speed driving is instantaneously increased due to an external factor and the rotational speed of the motor 11 falls below a predetermined rotational speed (for example, V2 rpm), the motor driver 13 starts an operation for switching the conduction method from the 180-degree conduction to the 120-degree conduction, as described above.

However, when the load continues to be applied and the motor 11 is rotated in a direction (0 rpm or less: hereinafter, may be referred to as "reverse rotation") reverse to a target rotational direction before the conduction method has been switched into the 120-degree conduction, the reverse rotational speed is a predetermined rotational speed (for example, minus V2 rpm) or less, and the motor driver 13 detects this reverse rotational speed; the motor driver 13 starts a protective operation for protecting the motor 11.

This is because in the 180-degree conduction method for generating a drive waveform of a sine wave on the basis of the previous signal transmitted from a hall element 15 (see FIG. 7: one example of magnetic sensor), the rotation of the motor 11 in the reverse direction causes recognition of a current supplying order that is different from the previous current supplying order, and thus the drive waveform is not able to be generated. The motor driver 13 is able to detect the rotational speed of the motor 11 by using the hall element 15 that is built in the motor apparatus 10.

The protective operation for protecting the motor 11 is a short brake that stops the rotation of the motor 11, for example. When the rotation of the motor 11 is reduced by this protective operation to "0" or an extremely low speed that is able to be approximated by zero, the protective operation is released and the rotation of the motor 11 is recovered.

On the other hand, during this protective operation performed by the motor driver 13, the motor apparatus 10 is not able to be driven even when the controller 12 transmits a speed command to the motor driver 13, thereby leading to an increase in a deviation (the number of speed command counts—the number of encoder signal counts) in the rotational position control of the motor 11.

Therefore, control for canceling this deviation in the rotational position control operates simultaneously with a release of the above-mentioned protective operation, and thus the motor 11 rapidly accelerates as illustrated in FIG. 6 so as to instantaneously increase flow volume per unit time. Furthermore, when the pump system 30 is in a heavy load state during this rapid acceleration, there exists the possibility that the tube 2 is broken due to a rapid pressure rise.

Thus, in the motor drive controlling apparatus according to the embodiment, the controller 12 is configured as described below so that it is possible to safely control operations of the motor 11 in a rotational state that is not in conformity with a commanded rotational state due to an external factor.

Figure 7:
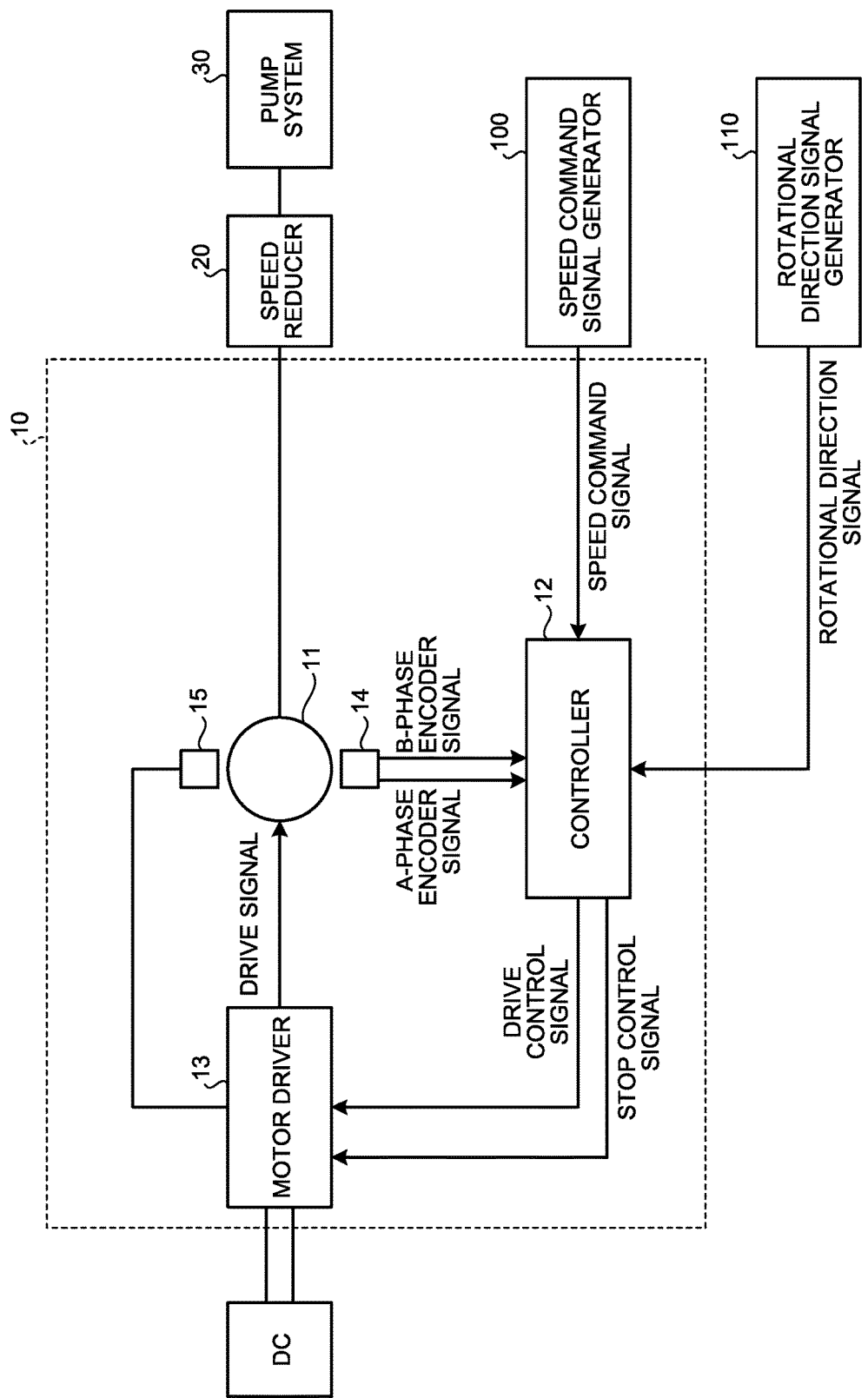
FIG. 7 is a block diagram illustrating a configuration example of the motor apparatus illustrated in FIG. 2.

FIG. 7 is a block diagram illustrating a configuration example of the motor apparatus 10 illustrated in FIG. 2. As illustrated in FIG. 7, the motor apparatus 10 includes the motor 11, the controller 12, the motor driver 13, the encoder 14 (one example of position detector), and the hall element 15 (one example of magnetic sensor).

Details will be mentioned later, the motor drive controlling apparatus includes: (i) the controller 12 that generates and outputs a drive control signal, in response to an input of a speed command signal and a rotational direction signal; (ii) the motor driver 13 that generates a drive signal and outputs the generated drive signal to the motor 11, in response to an input of the drive control signal; and (iii) the encoder 14 that detects a rotational position of the motor 11 and outputs an encoder signal (one example of detection signal) that is based on this detection result. The controller 12 includes: (a) a measurement unit that detects, on the basis of the encoder signal, a time point at which a rotational state of the motor 11 becomes, caused by an external factor, a different state that is different from a commanded rotational state based on a combination of the speed command signal and the rotational direction signal, and measures a movement amount from a rotational position at the time point at which the rotational state of the motor 11 becomes the above-mentioned different state; and (b) a transmitting unit that transmits, to the motor driver 13, a stop control signal for stopping an output of the drive signal, when the movement amount and an outputting state of the drive control signal satisfy a predetermined condition.

The motor 11 is connected to the pump system 30 via the speed reducer 20. The motor 11 is a three-phase brushless DC motor, for example. The motor drive controlling apparatus, which includes the controller 12 and the motor driver 13, controls the drive of the motor 11. The motor drive controlling apparatus may further include the encoder 14 and the hall element 15.

The controller 12 is connected to a speed command signal generator 100 and a rotational direction signal generator 110 that are external devices. The controller 12 is constituted of a micro processing unit (MPU), for example. To the controller 12, a speed command signal is input from the speed command signal generator 100 and a rotational direction signal is input from the rotational direction signal generator 110, and the controller 12 generates a drive control signal on the basis of the input speed command signal and the input rotational direction signal.

This speed command signal is a signal that is generated by the speed command signal generator 100, and includes command information for specifying a target rotational speed of the motor 11. Specifically, the speed command signal is a pulse signal whose number of counts is the target number of rotational steps, and whose number of counts per unit time is a target rotational speed.

The speed command signal generator 100 generates, as the speed command signal, a clock signal having a frequency according to the target rotational speed by using the pulse frequency modulation (PFM), for example, and outputs the generated clock signal to the controller 12.

The rotational direction signal generator 110 inputs the rotational direction signal to the controller 12, and the controller 12 controls the rotational direction of the motor 11 on the basis of the input rotational direction signal. The rotational direction signal includes command information for specifying a target rotational direction (hereinafter, may be referred to as "positive direction") of the motor 11. Specifically, the rotational direction signal is a digital signal having a value that differs between a case where the target rotational direction is a clockwise (CW) direction and a case where the target rotational direction is a counterclockwise (CCW) direction.

The controller 12 uses the PWM to generate, as a drive control signal, a PWM signal for causing the motor 11 to rotate at a rotational speed corresponding to a clock signal, for example. This drive control signal includes a control signal for causing the motor 11 to rotate in a rotational direction that is based on the rotational direction signal, as well as the PWM signal.

Furthermore, the controller 12 decides a commanded rotational state of the motor 11 by using a combination of the speed command signal and the rotational direction signal. When the speed command signal is larger than "0", the motor 11 is decided to be in a drive state, and the rotational direction signal is "0" or "1" in this case and a commanded rotational state of the motor 11 is decided to be "CW rotation" or "CCW rotation". For example, the command is "CCW rotation" when the rotational direction signal is zero, and the command is "CW rotation" when the rotational direction signal is one.

On the other hand, the motor 11 is decided to be in a hold state when the speed command signal is zero, and the rotational direction signal is not used.

The motor driver 13 is connected to a direct-current power supply DC, and generates a drive signal caused by an input of the drive control signal generated by the controller 12, so as to output the drive signal to the motor 11. The motor driver 13 has an inverter circuit and a pre-drive circuit that is an analog integrated circuit, for example.

The inverter circuit outputs to the motor 11 a drive signal on the basis of the output signal output from the pre-drive circuit, and supplies a current to three armature coils constituting the motor 11. For example, a series circuit constituted of two switching elements that are arranged on respective both ends of the direct-current power supply DC is arranged in the inverter circuit for each of three phases (U phase, V phase, and W phase) of an armature coil. In each series circuit of the two switching elements, a terminal of each phase of the motor 11 is connected with a connection point where the corresponding two switching elements are connected with each other.

The pre-drive circuit generates an output signal for driving the inverter circuit under the control of a drive control signal input from the controller 12, and outputs the generated output signal to the inverter circuit. This output signal includes six types of switching signals, which correspond to the respective switching elements of the inverter circuit, for example. When output signals are output to the inverter circuit, the switching elements corresponding to the output signals are turned on and off, so as to output the drive signal to the motor 11, and electric power is supplied to each phase of the motor 11.

Output timings of the switching signals that are output to the inverter circuit differ between the 120-degree conduction method and the 180-degree conduction method. Therefore, in the present embodiment, the pre-drive circuit of the motor driver 13 controls a conduction method of the motor 11.

The encoder 14 is one example of a position detector that detects a rotational position of the motor 11 (rotor 32). The encoder 14 outputs a pulse signal according to a speed command signal (clock signal), and further outputs to the controller 12 a detection signal (encoder signal) based on the number of counts of the output pulse signal.

When the motor 11 is rotating, the encoder 14 alternately outputs a signal from an A phase and a signal from a B phase having the phase that is different from the phase of the A phase by approximately an angle of 90 degrees. A measurement unit 41 (see FIG. 8) constituting the controller 12 counts, by using a counter, state changes in rising/falling of an output waveform of the A phase and state changes in rising/falling of an output waveform of the B phase, so as to measure the number of actual rotational steps, a rotational direction, and a rotational speed.

The hall element 15 is one example of a magnetic sensor that detects a position of a magnetic pole in the motor 11 (rotor 32), and outputs a position signal (hall signal) based on this detection result to the pre-drive circuit of the motor driver 13. The pre-drive circuit adjusts timings of switching between ON and OFF operations of the switching elements in the inverter circuit on the basis of the received hall signal.

The pre-drive circuit detects the rotational speed of the motor 11 on the basis of the state changes of the received hall signal so as to switch a conduction method of the motor 11. A hall integrated circuit (hall IC) may be used instead of the hall element 15.

The controller 12 generates a drive control signal (PWM signal) on the basis of the speed command signal (clock signal) and the encoder signal that is output from the encoder 14, and outputs the generated drive control signal to the motor driver 13. The controller 12 compares the number of counts of the clock signal (the number of target rotational steps) with the number of counts of the encoder signal (the number of actual rotational steps) while the input clock signal is causing the motor 11 to rotate, for example.

When both of the number of counts of the clock signal and that of the encoder signal are different from each other after adjusting a ratio between the numbers of the counts, the controller 12 generates a PWM signal whose duty ratio is changed so that both of the numbers of counts equal to each other, and outputs the generated PWM signal to the motor driver 13. The controller 12 may perform a control for maintaining the rotational speed of the motor 11 by using a signal output from the hall element 15, instead of the encoder signal output from the encoder 14, while the input clock signal causes the motor 11 to rotate.

Meanwhile, the pre-drive circuit of the motor driver 13 of the motor apparatus 10 is provided with the above-mentioned protective function that protects the motor 11 when the motor 11 rotates in the reverse direction due to load caused by an external factor. The pre-drive circuit detects an actual rotational direction and an actual rotational speed of the motor 11 on the basis of a hall signal transmitted from the hall element 15.

When detecting on the basis of the hall signal that the motor 11 rotates in a rotational direction (hereinafter, may be referred to as "reverse direction") reverse to the target rotational direction and the rotational speed in the reverse direction is the predetermined rotational speed or more (in other words, rotational speed in positive direction is predetermined minus rotational speed or less), the pre-drive circuit performs a protective operation for protecting the motor 11.

Here, in the present embodiment, when the motor 11 rotates in a reverse direction with respect to the target rotational direction, and when a movement amount from a time point at which the motor 11 started to rotate in the reverse direction and an outputting state of the drive control signal satisfy a predetermined condition indicating a heavy load state, the controller 12 transmits to the motor driver 13 a stop control signal for stopping the output of the drive signal.

Thus, even when an external factor causes the rotational state of the motor 11 to turn into not the commanded rotational state but the protective operation before the conduction method has switched from the 180-degree conduction method into the 120-degree conduction method, it is possible to suppress a breakage in the tube 2 due to a rapid pressure rise caused by rapid acceleration of the motor 11. Therefore, according to the present embodiment, it is possible to safely control operations of the motor 11 in a rotational state that is not in conformity with a commanded rotational state due to an external factor.

Figure 8:
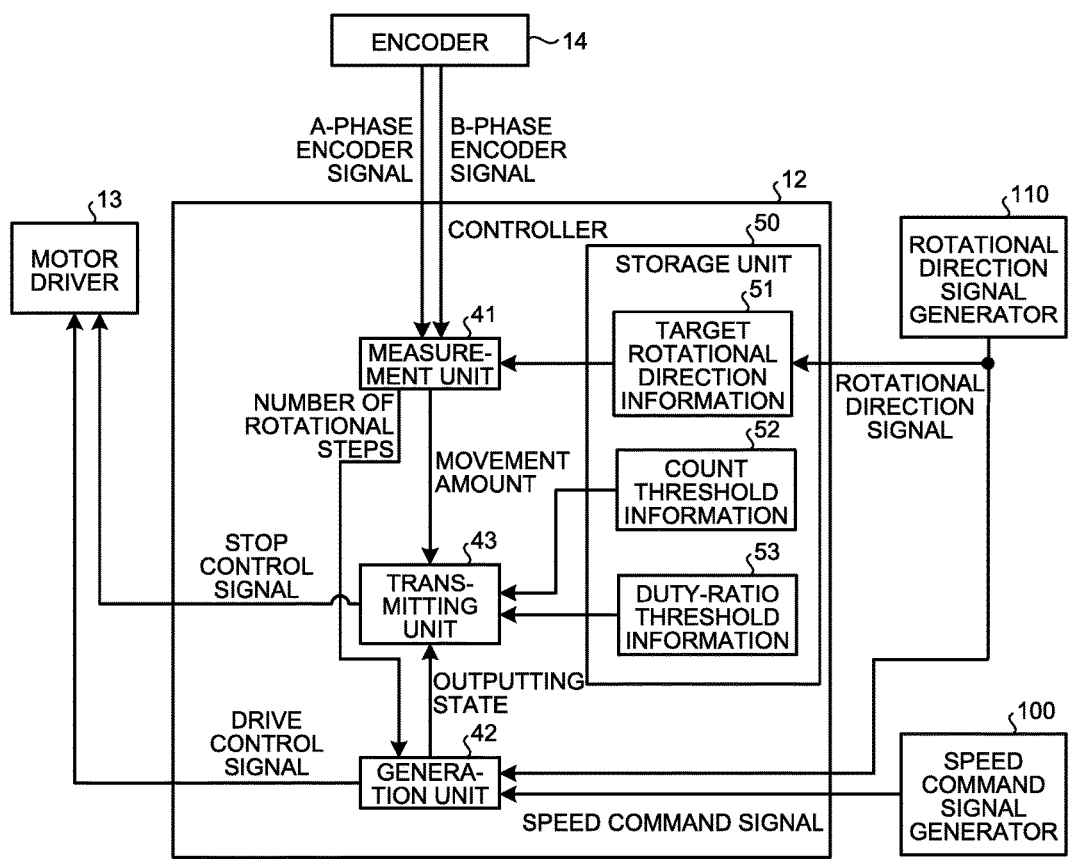
FIG. 8 is a block diagram illustrating a configuration example of a controller according to the embodiment.

FIG. 8 is a block diagram illustrating a configuration example the controller 12 according to the embodiment. The controller 12 includes the measurement unit 41, a generation unit 42, a transmitting unit 43, and a storage unit 50. The storage unit 50 stores target rotational direction information 51, count threshold information 52, and duty-ratio threshold information 53. The transmitting unit 43 includes a timer.

The storage unit 50 receives a rotational direction signal from the rotational direction signal generator 110, and stores the target rotational direction information 51 that is information on a target rotational direction (CW direction or CCW direction) of the motor 11. The measurement unit 41 measures a reverse count obtained by counting a movement amount from a rotational position at which the motor 11 started to rotate in the reverse direction, on the basis of the target rotational direction information 51 and an A-phase encoder signal and a B-phase encoder signal transmitted from the encoder 14. This method for measuring the reverse count will be mentioned later.

The generation unit 42 receives a speed command signal from the speed command signal generator 100 and further receives a rotational direction from the rotational direction signal generator 110, and generates a drive control signal on the basis of the received speed command signal, the received rotational direction signal, and the number of actual rotational steps that is counted by the measurement unit 41 by using the encoder signal. The generation unit 42 transmits the generated drive control signal to the motor driver 13. The generation unit 42 transmits an outputting state of the drive control signal to the transmitting unit 43. This outputting state of the drive control signal is a duty ratio of the drive control signal (PWM signal), for example. As described later, when the duty ratio of the PWM signal is a predetermined ratio or more, the transmitting unit 43 transmits a stop control signal to the motor driver 13.

The transmitting unit 43 compares the reverse count measured by the measurement unit 41 with a count threshold (one example of specified value) stored in the count threshold information 52 of the storage unit 50. This count threshold is one example of a predetermined threshold with respect to a movement amount from a rotational position at which the motor 11 started to rotate in the reverse direction.

Furthermore, the transmitting unit 43 compares a duty ratio of a PWM signal transmitted from the generation unit 42 with a duty ratio threshold included in the duty-ratio threshold information 53 stored in the storage unit 50.

When the reverse count is the predetermined count threshold or more and further the duty ratio of the PWM signal is the predetermined duty ratio threshold or more, the transmitting unit 43 determines that the pump system 30 is in a heavy load state. Thus, the transmitting unit 43 transmits the above-mentioned stop control signal to the motor driver 13.

Figure 9:
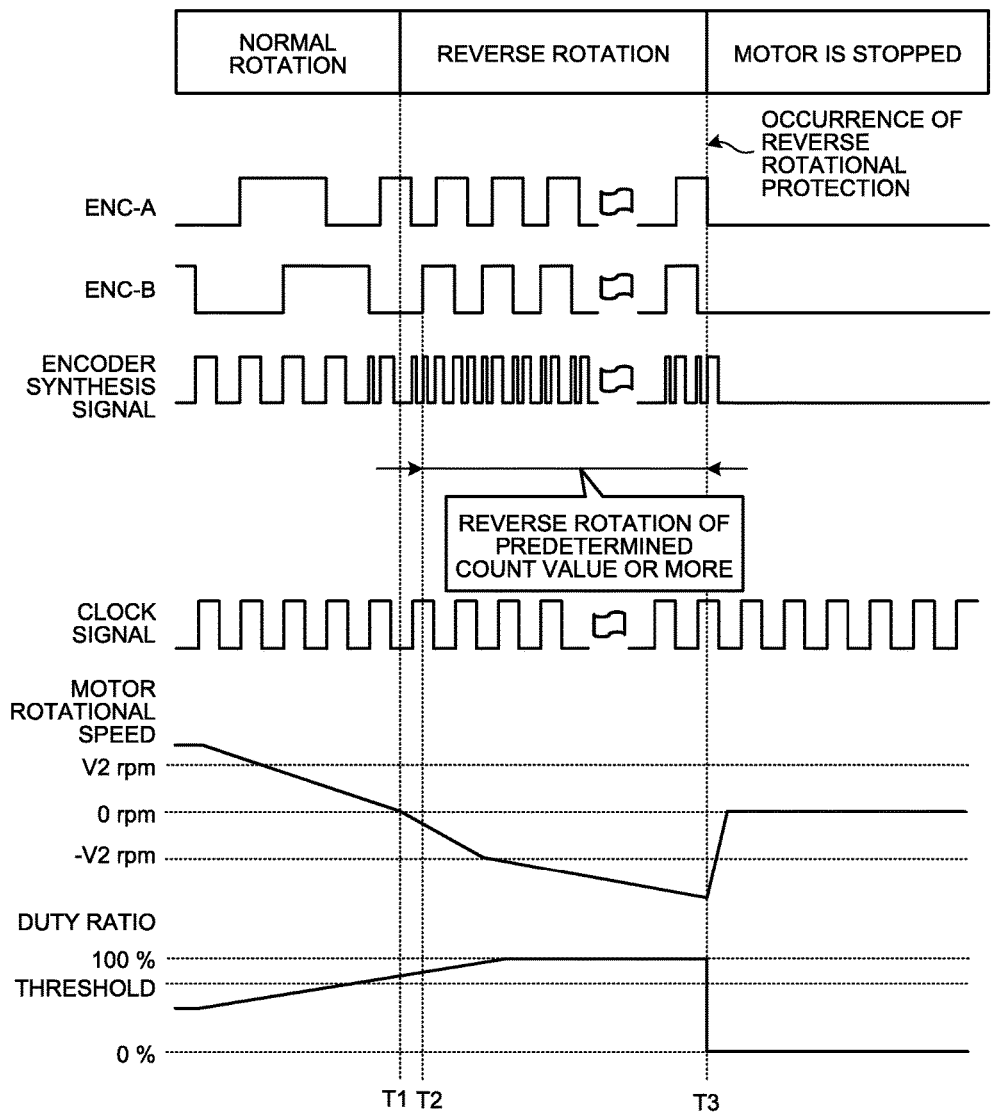
FIG. 9 is a timing diagram illustrating one example of a relation during a motor driving period between signal elements of a motor drive controlling apparatus according to the embodiment.

FIG. 9 is a timing diagram illustrating one example of a relation during a motor driving period between signal elements of the motor drive controlling apparatus according to the embodiment. In the example illustrated in FIG. 9, the motor 11 is being driven, and thus the speed command generator 100 outputs a clock signal. Furthermore, in the example illustrated in FIG. 9, a case is illustrated in which a target rotational direction specified by the motor 11 by using a rotational direction signal is the CCW direction.

Therefore, as illustrated in FIG. 9, "0" (Low signal) is output as a value of a B-phase encoder signal (ENC-B), next "1" (High signal) is output as a value of an A-phase encoder signal (ENC-A), and then "1" is output as a value of the B-phase encoder signal. Subsequently, "0" is output as a value of the A-phase encoder signal, the A-phase encoder signal and the B-phase encoder signal are alternately output thereafter in this predetermined order.

On the other hand, when the target rotational direction of the motor 11 is the CW direction, "0" is output as a value of the A-phase encoder signal, next "1" is output as a value of the B-phase encoder signal, and then "1" is output as a value of the A-phase encoder signal. Subsequently, "0" is output as a value of the B-phase encoder signal, the A-phase encoder signal and the B-phase encoder signal are alternately output thereafter in this predetermined order. These outputs of the A-phase encoder signal and the B-phase encoder signal are synthesized into an encoder synthesis signal.

When the motor 11 maintains a predetermined rotational speed, the encoder signals (A-phase and B-phase encoder signals), which are alternately output, are output in accordance with a speed command signal (clock signal). In the example illustrated in FIG. 9, the motor 11 is driven by the 180-degree conduction method in the above-mentioned state.

However, when load caused by an external factor increases and the rotational speed of the motor 11 falls below a target rotational speed, the encoder signals output from the encoder 14 become behind the clock signal. Furthermore, when the motor 11 rotates in the reverse direction at a time point T1, encoder signals that are not according to a predetermined order are output.

In the example illustrated in FIG. 9, when the motor 11 rotates in the reverse direction after "1" (value of A-phase encoder signal) is output, "1" (value of B-phase encoder signal) that is in the next order is not output, "0" (value of A-phase encoder signal) is output instead. Furthermore, when the motor 11 continues rotating in the reverse direction, "1" (value of B-phase encoder signal) indicating that the reverse rotation is continued at a time point T2 is output after "0" (value of A-phase encoder signal) was output.

When the reverse rotation is continued, the above-mentioned reverse count, which is measured from the time point T2, reaches a predetermined movement amount at a time point T3. A reason for starting to measure the reverse count not from the time point T1 but from the time point T2 is to except effects of fluctuation in the rotational direction when the motor 11 rotates at an extremely low rotational speed, namely occurrence of chattering phenomena. Details of a method for counting the reverse count performed by the measurement unit 41 will be mentioned later.

In a case where the reverse count reaches a predetermined count value or more, when the duty ratio of the PWM signal is a predetermined ratio (for example, 80% or more), the transmitting unit 43 transmits to the motor driver 13 a stop control signal for stopping outputting of the drive signal in order to protect the motor 11 against the reverse rotation. Here, in the example illustrated in FIG. 9, the duty ratio of the PWM signal is 100% at the time point T3, and thus the above-mentioned condition is satisfied.

Therefore, in the example illustrated in FIG. 9, the transmitting unit 43 transmits a stop control signal to the motor driver 13 at the time point T3, and thus the rotation of the motor 11 is stopped. In this manner, when the motor 11 moves by a predetermined amount from a position at which the motor 11 started to rotate in the reverse direction and the duty ratio of the PWM signal is a predetermined ratio or more, the pump system 30 is determined to be in a heavy load state.

In the present embodiment, the stop control signal is transmitted to the motor driver 13 so as to stop the motor 11, so that it is possible to suppress a breakage in the tube 2 due to a rapid pressure rise caused by rapid acceleration of the motor 11.

Figure 10:
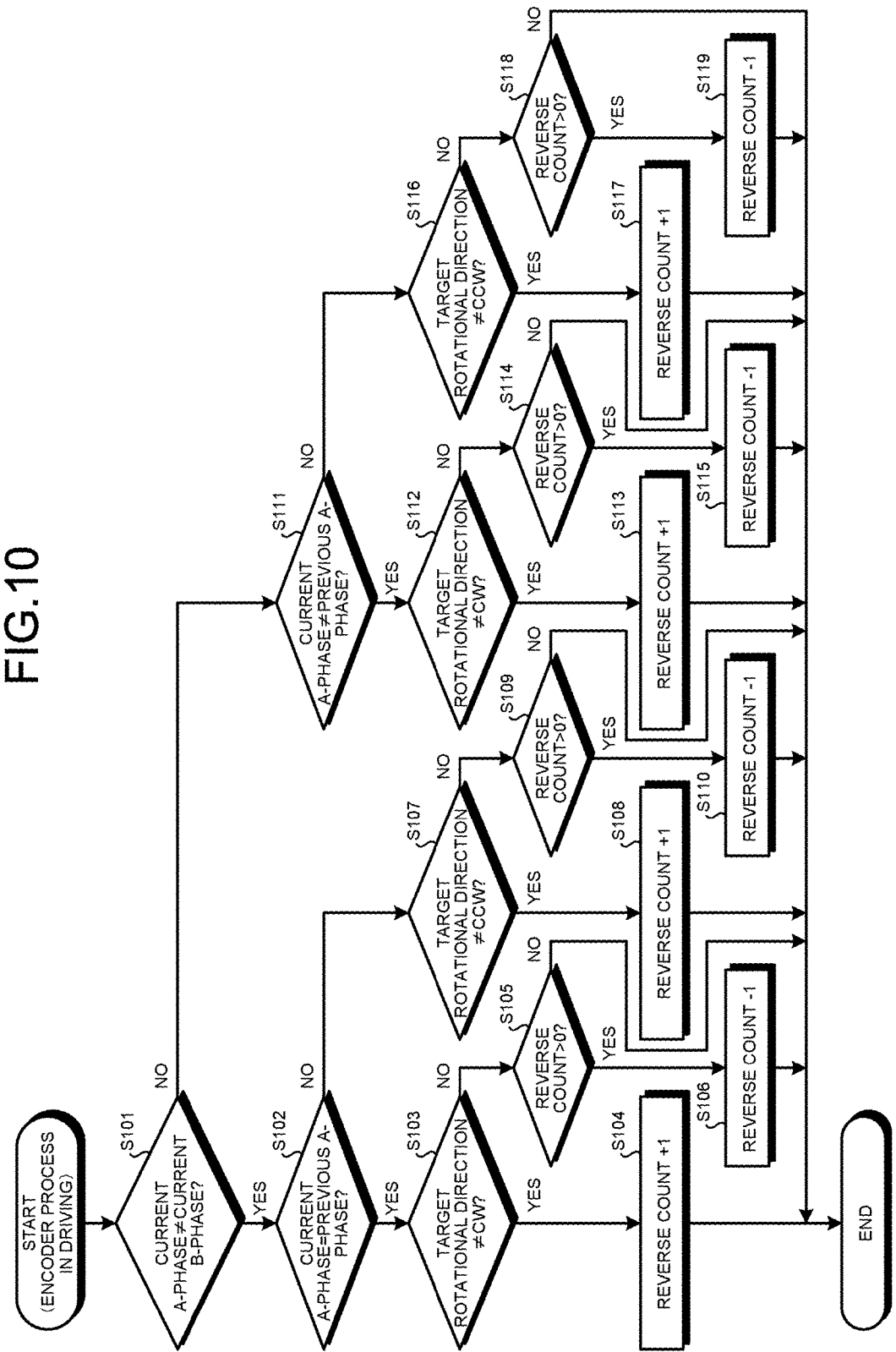
FIG. 10 is a flowchart illustrating a process for measuring a reverse count during a motor driving period according to the embodiment.
Figure 11:
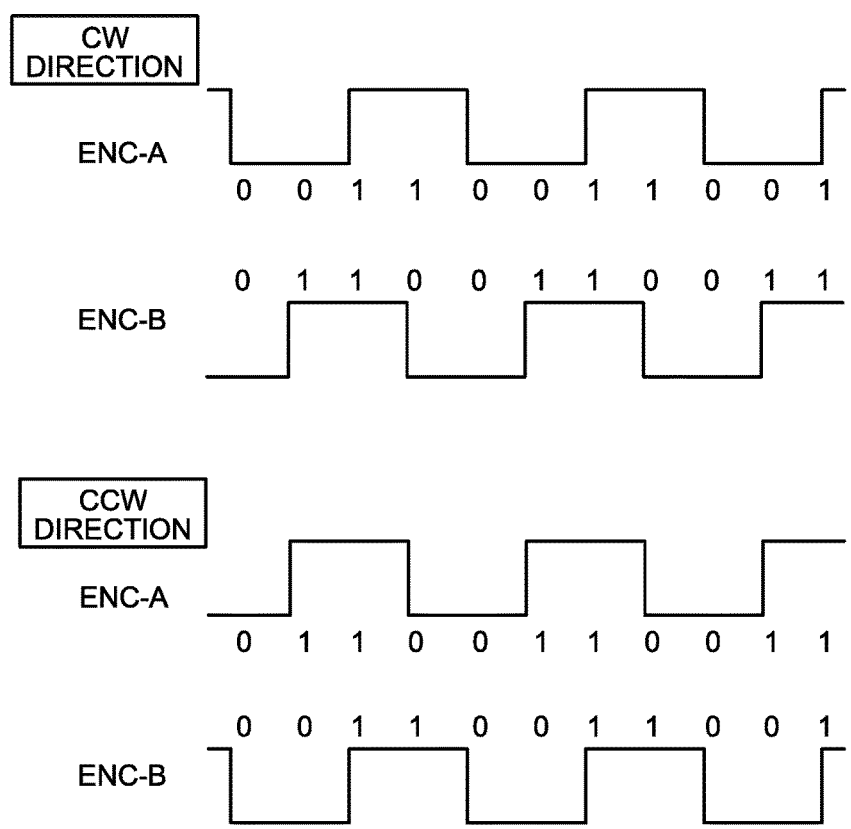
FIG. 11 is a diagram schematically illustrating outputting states of encoder signals in clockwise (CW) and counterclockwise (CCW) directions according to the embodiment.

Next, a process for measuring the reverse count will be explained with reference to FIGS. 10 and 11. FIG. 10 is a flowchart illustrating the process for measuring the reverse count during a motor driving period according to the embodiment. FIG. 11 is a diagram schematically illustrating outputting states of encoder signals in the CW and CCW directions according to the embodiment. The process for measuring the reverse count illustrated in FIG. 10 is performed at each time when the measurement unit 41 receives a change in a state of the A-phase encoder signal or the B-phase encoder signal.

As illustrated in FIG. 10, the measurement unit 41 determines whether or not a current value of the A-phase encoder signal and that of the B-phase encoder signal are different from each other (Step S101). In other words, the measurement unit 41 determines whether or not the current value of the A-phase encoder signal is "1" and that of the B-phase encoder signal is "0", and the current value of the A-phase encoder signal is "0" and that of the B-phase encoder signal is "1". When this condition is satisfied (Step S101: Yes), the measurement unit 41 determines whether or not the current value of the A-phase encoder signal equals to a value of the A-phase encoder signal in the previous process (Step S102).

Next, when the current value of the A-phase encoder signal equals to the value of the A-phase encoder signal in the previous process (Step S102: Yes), the measurement unit 41 determines whether or not a target rotational direction is not the CW direction on the basis of the target rotational direction information 51 (Step S103). When the target rotational direction is not the CW direction (Step S103: Yes), "1" is added to the reverse count (Step S104), and the process is terminated.

In other words, as illustrated in FIG. 11, when "Step S101: Yes" and "Step S102: Yes" are satisfied, the rotational direction of the motor 11 is the CW direction. When "Step S103: Yes" is satisfied, the target rotational direction is the CCW direction, and thus "1" is added to the reverse count.

When the determination condition of Step S103 is not satisfied (Step S103: No), in other words, when the rotational direction of the motor 11 is the CW direction that is the same as the target rotational direction, the measurement unit 41 determines whether or not the reverse count is larger than "0" (Step S105). When the reverse count is larger than "0" (Step S105: Yes), "1" is subtracted from the reverse count (Step S106), and the process is terminated; otherwise (Step S105: No), the process is terminated without any change.

When the determination condition of Step S102 is not satisfied (Step S102: No), the measurement unit 41 determines whether or not the target rotational direction is not the CCW direction on the basis of the target rotational direction information 51 (Step S107). When the target rotational direction is not the CCW direction (Step S107: Yes), "1" is added to the reverse count (Step S108), and the process is terminated.

In other words, as illustrated in FIG. 11, when "Step S101: Yes" and "Step S102: No" are satisfied, the rotational direction of the motor 11 is the CCW direction. When "Step S107: Yes" is satisfied, the target rotational direction is the CW direction, and thus "1" is added to the reverse count.

When the determination condition of Step S107 is not satisfied (Step S107: No), in other words, when the rotational direction of the motor 11 is the CCW direction that is the same as the target rotational direction, the measurement unit 41 determines whether or not the reverse count is larger than "0" (Step S109). Here, when the reverse count is larger than "0" (Step S109: Yes), "1" is subtracted from the reverse count (Step S110), and the process is terminated; otherwise (Step S109: No), the process is terminated without any change.

Furthermore, the determination condition of Step S101 is not satisfied (Step S101: No), the measurement unit 41 determines whether or not the current value of the A-phase encoder signal equals to a value of the A-phase encoder signal in the previous process (Step S111).

Next, the current value of the A-phase encoder signal does not equal to the value of the A-phase encoder signal in the previous process (Step S111: Yes), the measurement unit 41 determines whether or not the target rotational direction is not the CW direction on the basis of the target rotational direction information 51 (Step S112). When the target rotational direction is not the CW direction (Step S112: Yes), "1" is added to the reverse count (Step S113), and the process is terminated.

In other words, as illustrated in FIG. 11, when "Step S101: No" and "Step S111: Yes" are satisfied, the rotational direction of the motor 11 is the CW direction. When "Step S112: Yes" is satisfied, the target rotational direction is the CCW direction, and thus "1" is added to the reverse count.

When the determination condition of Step S112 is not satisfied (Step S112: No), in other words, when the rotational direction of the motor 11 is the CW direction that is the same as the target rotational direction, the measurement unit 41 determines whether or not the reverse count is larger than "0" (Step S114). Here, when the reverse count is larger than "0" (Step S114: Yes), "1" is subtracted from the reverse count (Step S115), and the process is terminated; otherwise (Step S114: No), the process is terminated without any change.

When the determination condition of Step S111 is not satisfied (Step S111: No), the measurement unit 41 determines whether or not the target rotational direction is not the CCW direction on the basis of the target rotational direction information 51 (Step S116). When the target rotational direction is not the CCW direction (Step S116: Yes), "1" is added to the reverse count (Step S117), and the process is terminated.

In other words, as illustrated in FIG. 11, when "Step S101: No" and "Step S111: No" are satisfied, the rotational direction of the motor 11 is the CCW direction. When "Step S116: Yes" is satisfied, the target rotational direction is the CW direction, and "1" is added to the reverse count.

When the determination condition of Step S116 is not satisfied (Step S116: No), in other words, when the rotational direction of the motor 11 is the CCW direction that is the same as the target rotational direction, the measurement unit 41 determines whether or not the reverse count is larger than "0" (Step S118). Here, when the reverse count is larger than "0" (Step S118: Yes), "1" is subtracted from the reverse count (Step S119), and the process is terminated; otherwise (Step S118: No), the process is terminated without any change.

In this manner, the reverse count is measured on the basis of an encoder signal that is output from the encoder 14 having a higher resolution than the hall element 15, so that it is possible to detect the reverse rotation of the motor 11 immediately after the motor 11 has rotated in the reverse direction.

Figure 12:
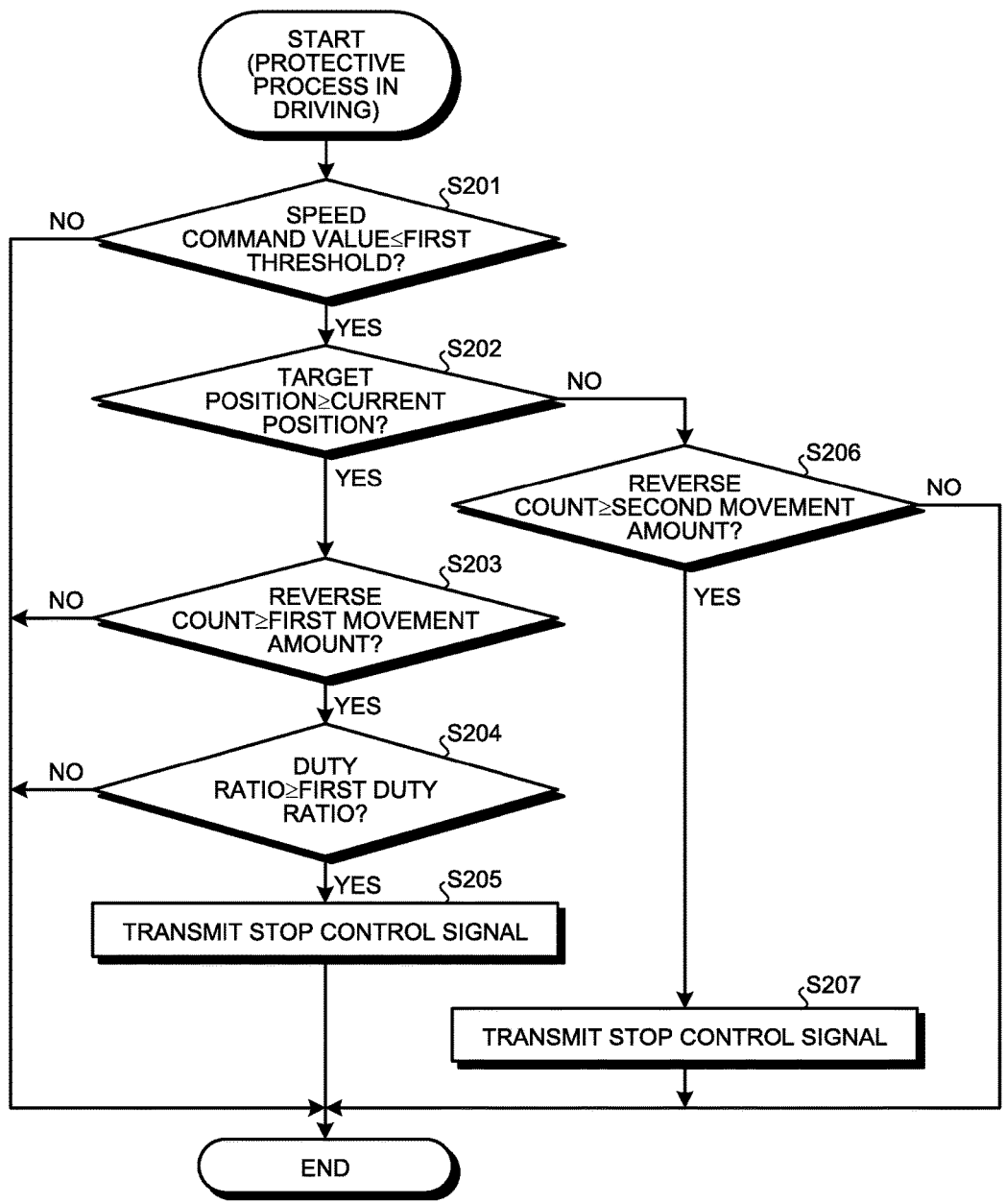
FIG. 12 is a flowchart illustrating a process for transmitting a stop control signal during motor driving period according to the embodiment.

FIG. 12 is a flowchart illustrating a process for transmitting the stop control signal during motor driving period according to the embodiment. The process for transmitting the stop control signal illustrated in FIG. 12 is periodically performed. Note that this process is not performed during the protective operation performed by the motor driver 13.

Details will be mentioned later, the measurement unit 41 detects, on the basis of the encoder signal (one example of detection signal), a time point at which a rotation of the motor 11 is, caused by an external factor, switched into a reverse direction that is reverse to a target rotational direction while the speed command signal and the rotational direction signal are being input, and measures a movement amount of the motor 11 in the reverse direction from a rotational position of the motor 11 at the time point at which the rotation of the motor 11 is switched, on the basis of the encoder signal as the movement amount. The transmitting unit 43 transmits the stop control signal to the motor driver 13 when the movement amount is a predetermined first movement amount or more and the duty ratio of the PWM signal is a predetermined first duty ratio or more.

The transmitting unit 43 does not transmit the stop control signal to the motor driver 13, when the movement amount is the first movement amount or more and the duty ratio of the PWM signal does not exceed the first duty ratio, in a state where a current rotational position of the motor 11 based on the encoder signal precedes a target rotational position based on the speed command signal while the speed command signal and the rotational direction signal are being input.

The transmitting unit 43 transmits the stop control signal to the motor driver 13, when the movement amount is equal to or more than a predetermined second movement amount that is the first movement amount or more, in a state where the current rotational position of the motor 11 precedes the target rotational position while the speed command signal and the rotational direction signal are being input, even when the duty ratio of the PWM signal does not exceed the first duty ratio. Furthermore, the transmitting unit 43 does not transmit the stop control signal to the motor driver 13 when the rotational speed of the motor 11 that is set by the speed command signal is a predetermined threshold or more.

As illustrated in FIG. 12, the transmitting unit 43 determines whether or not a speed command value commanded by the speed command signal is a predetermined first threshold or less (Step S201). When the speed command value is the first threshold or less (Step S201: Yes), the transmitting unit 43 determines whether or not a count value corresponding to a current position based on the encoder signal is equal to or less than a count value corresponding to a target position based on the speed command signal and the rotational direction signal (Step S202). When the determination condition of Step S201 is not satisfied (Step S201: No), the transmitting unit 43 regards the motor 11 as being in high speed rotation, and the process is terminated.

When the count value indicating the current position is equal to or less than the count value corresponding to the target position (Step S202: Yes), the transmitting unit 43 regards the motor 11 as going back from the target rotational position and moving in the reverse direction.

Next, the transmitting unit 43 determines whether or not the reverse count is equal to or more than a count value corresponding to the predetermined first movement amount (Step S203). This first movement amount is one example of a count threshold stored in the count threshold information 52.

When the reverse count is the first movement amount or more (Step S203: Yes), the transmitting unit 43 determines whether or not the duty ratio of the PWM signal is the predetermined first duty ratio or more (for example, duty ratio 80%: Step S204). This first duty ratio is one example of the duty ratio threshold stored in the duty-ratio threshold information 53. When the determination condition of Step S203 is not satisfied (Step S203: No), the process is terminated.

Next, when the duty ratio of the PWM signal is the first duty ratio or more (Step S204: Yes), the transmitting unit 43 transmits to the motor driver 13 the stop control signal for stopping the motor 11 (Step S205), and the process is terminated. When the determination condition of Step S204 is not satisfied (Step S204: No), the process is terminated.

When the determination condition of Step S202 is not satisfied (Step S202: No), the transmitting unit 43 regards the motor 11 as preceding the target rotational position. The transmitting unit 43 determines whether or not the reverse count is equal to or more than a count value corresponding to the predetermined second movement amount (Step S206). This second movement amount is another example of the count threshold stored in the count threshold information 52, and is a movement amount that is larger than the above-mentioned first movement amount (movement angle).

When the reverse count is the second movement amount or more (Step S206: Yes), the transmitting unit 43 transmits to the motor driver 13 the stop control signal for stopping the motor 11 (Step S207), and the process is terminated. When the determination condition of Step S206 is not satisfied (Step S206: No), the process is terminated.

As described above, in a state where the motor 11 goes back from a target rotational position and moves in the reverse direction, when the movement amount is the predetermined first movement amount or more and the duty ratio of the PWM signal is the first duty ratio or more, the transmitting unit 43 transmits a stop control signal to the motor driver 13 so as to stop the motor 11. Thus, it is possible to precisely detect a heavy load state so as to stop the motor 11.

In a state where the motor 11 precedes the target rotational position but moves in the reverse direction, when the movement amount is the predetermined first movement amount or more and the duty ratio of the PWM signal is the first duty ratio or more, the transmitting unit 43 transmits a stop control signal to the motor driver 13 so as to stop the motor 11.

In other words, even when the movement amount is the predetermined first movement amount or more, the transmitting unit 43 does not transmit the stop control signal to the motor driver 13 unless the duty ratio of the PWM signal is the first duty ratio or more. Thus, it is possible to cause the motor 11 to continue to drive when the motor 11 is not in a heavy load state.

Furthermore, in a state where the motor 11 precedes a target rotational position but moves in the reverse direction, when a movement amount is equal to or more than the predetermined second movement amount that is larger than the first movement amount, the transmitting unit 43 transmits a stop control signal to the motor driver 13 so as to stop the motor 11, regardless of the duty ratio of the PWM signal. Thus, even when the motor 11 is determined not to be in a heavy load state by the duty ratio, it is possible to stop the motor 11 by regarding a delivery amount of liquid as changing largely.

Furthermore, during high speed rotation (for example, more than V4 rpm) in which the speed command signal is a predetermined threshold (first threshold) or more, the drive of the motor 11 is not stopped. Thus, it is possible to omit redundant determinations in the controller 12, thereby leading to increase in processing ability of the controller 12.

Figure 13:
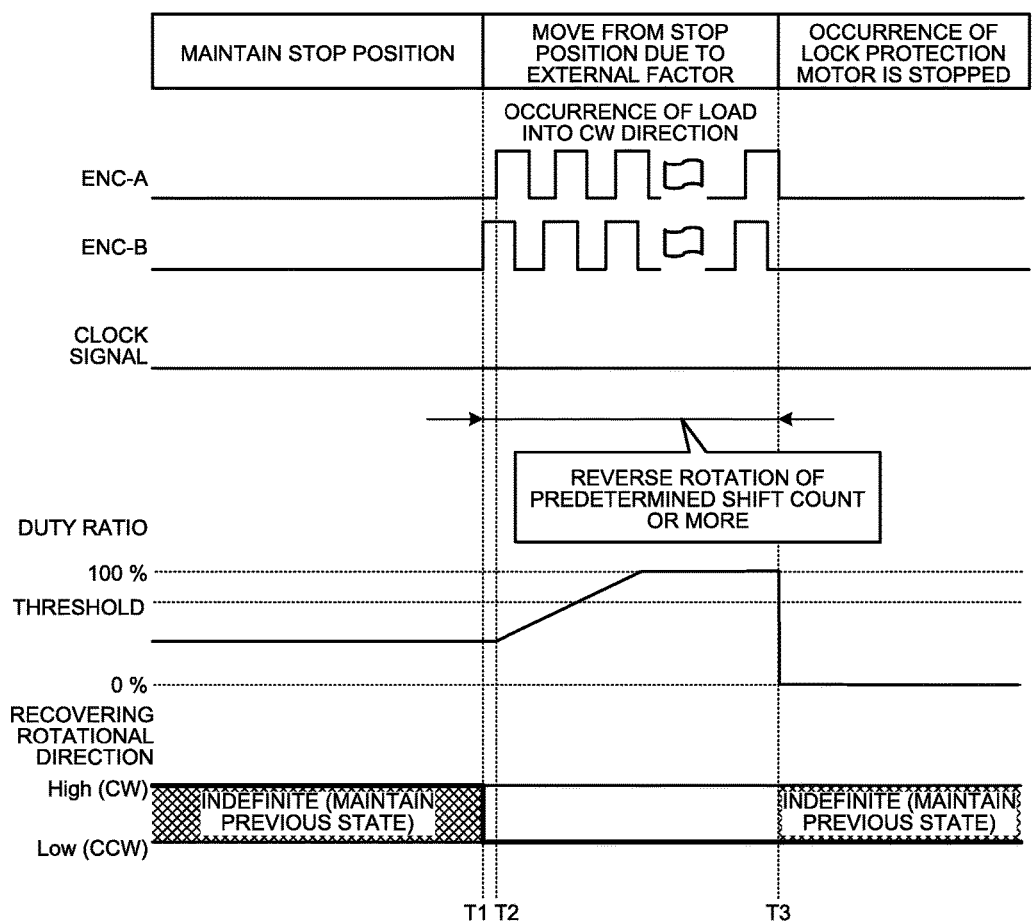
FIG. 13 is a timing diagram illustrating one example of a relation during a motor holding period between signal elements of the motor drive controlling apparatus according to the embodiment.

FIG. 13 is a timing diagram illustrating one example of a relation during a motor holding period between signal elements of the motor drive controlling apparatus according to the embodiment. In the example illustrated in FIG. 13, the speed command signal generator 100 outputs no clock signal because the motor 11 is in holding.

In the example illustrated in FIG. 13, when the motor 11 is rotated in either direction due to load caused by an external factor, the motor drive controlling apparatus drives the motor 11 in a recovering rotational direction (direction reverse to load) and controls the motor 11 so as to be held in the target rotational position.

In this manner, the control for holding the motor 11 in a predetermined rotational position may be referred to as a holding torque operation. This holding torque operation is performed for returning, to a stop position, the motor 11 whose rotational position at a stop is shifted due to an external factor, not only when the motor 11 is at a stop, but also when the controller 12 controls the motor 11 so that the motor 11 repeatedly rotates and stops and is intermittently driven so as to realize low speed rotation, for example.

The "recovering rotational direction" is a rotational direction that is included in the drive control signal and is for recovering the motor 11 to an original position by using the holding torque operation. Therefore, the motor 11 is to be rotated in a direction reverse to a direction in which load has occurred, and thus when load has occurred into the CW direction, the recovering rotational direction is the CCW direction, for example.

Furthermore, as illustrated in FIG. 13, the recovering rotational direction is "indefinite (maintaining previous state)" while the motor 11 is holding its stop position. This state is a state in which whether the recovering rotational direction is the CW direction or the CCW direction is not decided, and is a state in which the recovering rotational direction during the previous holding torque operation is merely held as the rotational direction.

In the example illustrated in FIG. 13, load occurs into the CW direction due to an external factor from the time point T1, and the motor 11 starts to rotate in the CW direction. The motor drive controlling apparatus performs the holding torque operation that increases the duty ratio from a time point corresponding to the predetermined number of two or more counts (in present example, time point T2 corresponding to second count) of the encoder 14 and drives the motor 11 in the recovering rotational direction (in this case, CCW direction).

However, in the present embodiment, even in a case where this holding torque operation is performed, when a shift amount of the motor 11 corresponds at the time point T3 to equal to or more than a predetermined shift count that is one example of a predetermined shift amount and the duty ratio of the drive control signal is a predetermined threshold or more, the motor drive controlling apparatus performs lock protection so as to stop the motor 11. Similarly to the case of the motor 11 in being driven, the transmitting unit 43 transmits a stop control signal to the motor driver 13 so as to perform this lock protection.

In this manner, the lock protection is performed when the shift amount of the motor 11 in the holding state exceeds a predetermined shift amount due to an external factor, so that it is possible to prevent rapid acceleration of the motor 11 when the external factor is released.

Figure 14:
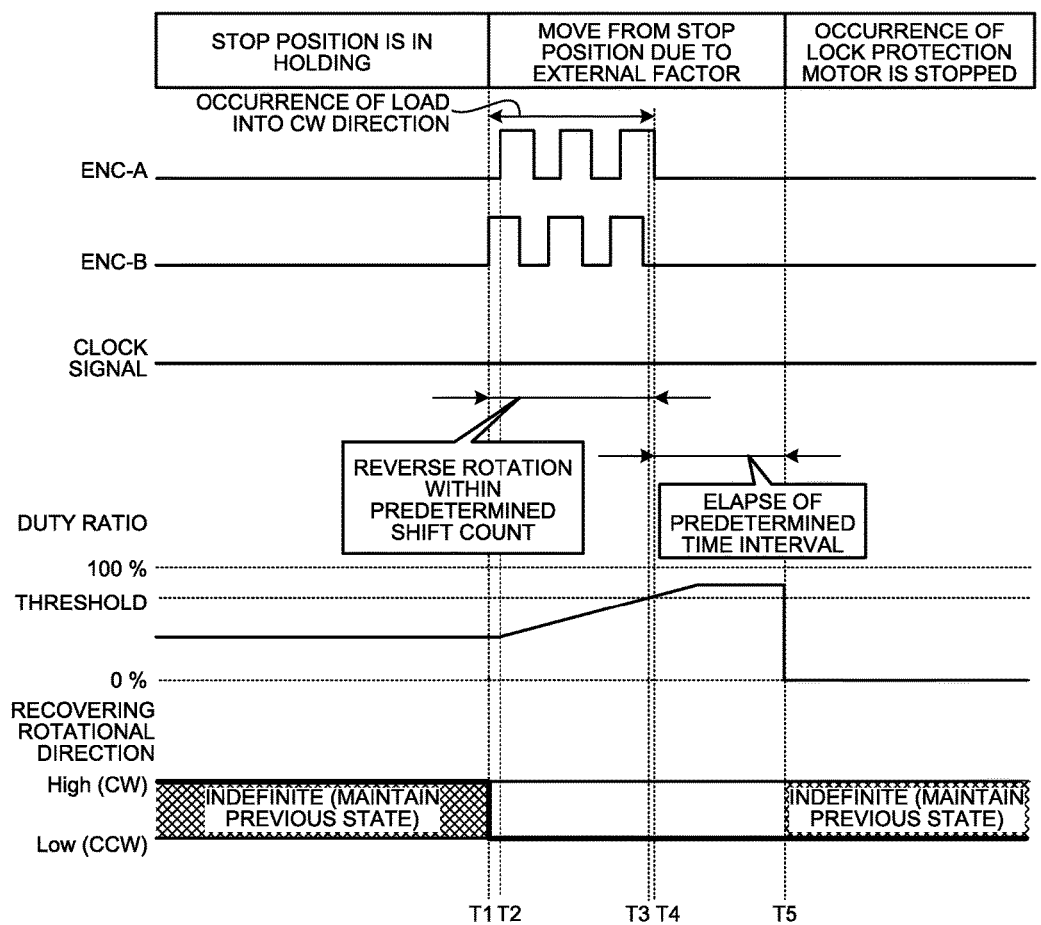
FIG. 14 is a timing diagram illustrating another example of the relation during a motor holding period between the signal elements of the motor drive controlling apparatus according to the embodiment.

FIG. 14 is a timing diagram illustrating another example of the relation during a motor holding period between the signal elements of the motor drive controlling apparatus according to the embodiment. The example illustrated in FIG. 14 is during the motor holding period, and thus the speed command signal generator 100 outputs no clock signal.

In the example illustrated in FIG. 14, load occurs into the CW direction due to an external factor from the time point T1, and the motor 11 starts to rotate in the CW direction. The motor drive controlling apparatus performs the holding torque operation that increases the duty ratio from a time point corresponding to the predetermined number of two or more counts (in present example, time point T2 corresponding to second count) of the encoder 14 and drives the motor 11 in the recovering rotational direction (in this case, CCW direction), and the rotation of the motor 11 is stopped within predetermined shift counts (time point T4).

However, in the present embodiment, when the duty ratio of the PWM signal has been kept equal to or more than a predetermined threshold from the time point T3 and a predetermined time interval (for example, time interval from time point T4 to time point T5) has elapsed from the time point T4 at which the encoder signals are changed, the motor drive controlling apparatus performs the lock protection so as to stop the motor 11.

In this manner, the lock protection is performed when a predetermined time interval has elapsed in a state where the duty ratio of the PWM signal is a predetermined threshold or more even when the shift amount of the motor 11 in the holding state, which is due to an external factor, is a predetermined shift amount or less, so that it is possible to prevent rapid acceleration of the motor 11 when the external factor is released.

Figure 15:
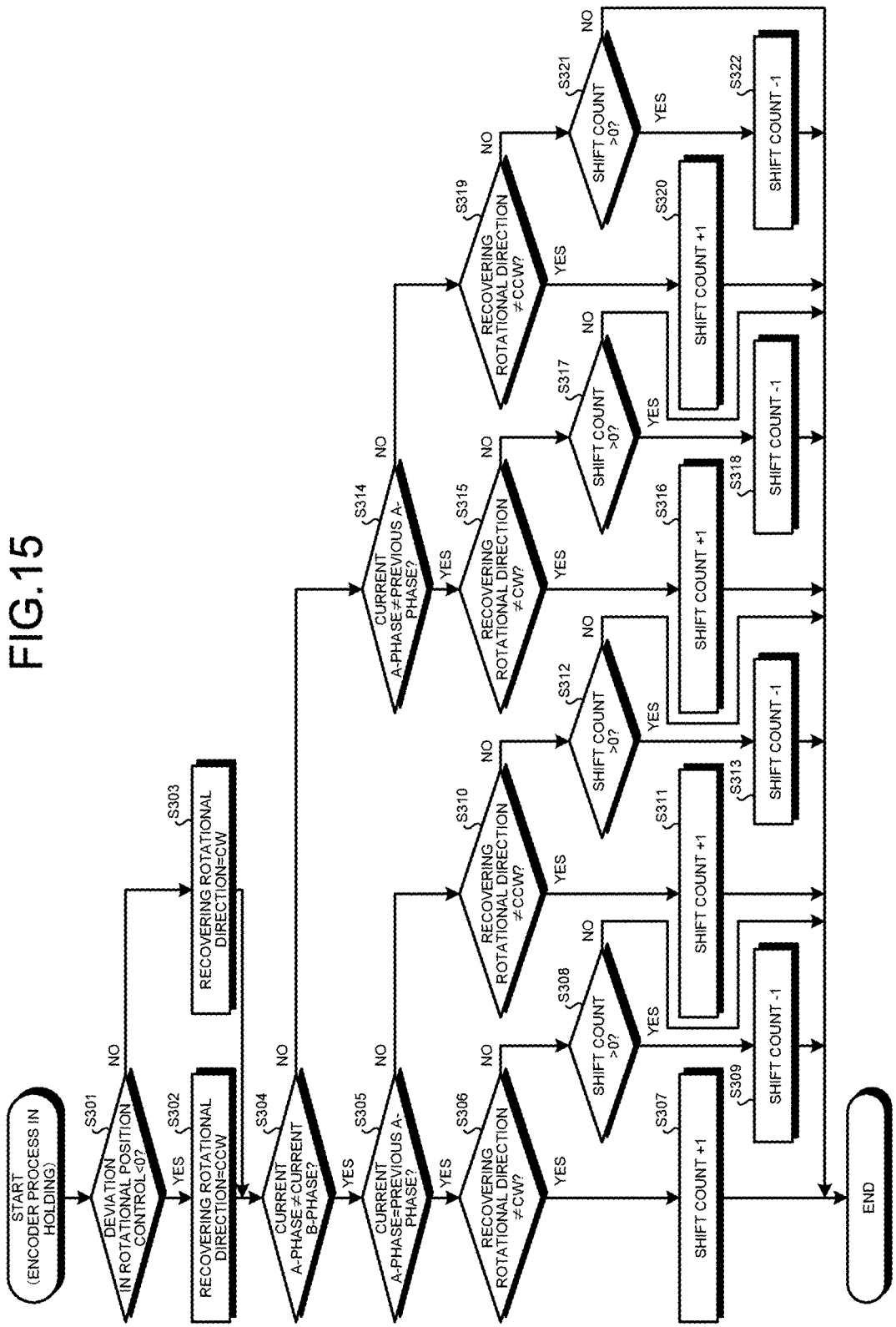
FIG. 15 is a flowchart illustrating a process for measuring a shift count during a motor holding period according to the embodiment.

FIG. 15 is a flowchart illustrating a process for measuring a shift count during a motor holding period according to the embodiment. The process for measuring the shift count illustrated in FIG. 15 is performed at each time when the measurement unit 41 receives a change in a state of the A-phase encoder signal or the B-phase encoder signal. The motor 11 has been stopped during the motor holding period, the speed command signal generator 100 outputs no speed command signal, and the measurement unit 41 does not use the rotational direction signal transmitted from the rotational direction signal generator 110, and thus a process is performed in which a load-applied rotational direction is determined by increase/decrease in the number of encoder signal counts, and a rotational direction reverse to the load-applied rotational direction is set to the recovering rotational direction that is used for returning the rotational position of the motor 11 to a stop position when the rotational position is shifted by an external factor.

As illustrated in FIG. 15, the measurement unit 41 determines whether or not a deviation in the rotational position control is smaller than "0" (Step S301). Here, the "deviation in rotational position control" means a value obtained by subtracting the number of encoder signal counts from the number of speed command counts, and the number of encoder signal counts is increased when load is applied in the CW direction, and thus the deviation in the rotational position control becomes negative. The number of encoder signal counts is reduced when load is applied in the CCW direction, and thus the deviation in the rotational position control becomes positive.

When the deviation in the rotational position control is smaller than "0" (Step S301: Yes), the measurement unit 41 sets the recovering rotational direction to the CCW direction (Step S302). When the determination condition of Step S301 is not satisfied (Step S301: No), the measurement unit 41 sets the recovering rotational direction to the CW direction (Step S303).

Next, the measurement unit 41 determines whether or not a current value of the A-phase encoder signal and that of the B-phase encoder signal are different from each other (Step S304). In other words, the measurement unit 41 determines whether or not the current value of the A-phase encoder signal is "1" and that of the B-phase encoder signal is "0", and the current value of the A-phase encoder signal is "0" and that of the B-phase encoder signal is "1". When this condition is satisfied (Step S304: Yes), the measurement unit 41 determines whether or not the current value of the A-phase encoder signal equals to a value of the A-phase encoder signal in the previous process (Step S305).

Next, when the current value of the A-phase encoder signal equals to the value of the A-phase encoder signal in the previous process (Step S305: Yes), the measurement unit 41 determines whether or not a recovering rotational direction is not the CW direction (Step S306). When the recovering rotational direction is not the CW direction (Step S306: Yes), "1" is added to the shift count (Step S307), and the process is terminated.

In other words, as illustrated in FIG. 11, when "Step S304: Yes" and "Step S305: Yes" are satisfied, the rotational direction of the motor 11 is the CW direction. When "Step S306: Yes" is satisfied, the recovering rotational direction is the CCW direction, and thus "1" is added to the shift count.

When the determination condition of Step S306 is not satisfied (Step S306: No), in other words, when the rotational direction of the motor 11 is the CW direction that is the same as the recovering rotational direction, the measurement unit 41 determines whether or not the shift count is larger than "0" (Step S308). When the shift count is larger than "0" (Step S308: Yes), "1" is subtracted from the shift count (Step S309), and the process is terminated; otherwise (Step S308: No), the process is terminated without any change.

When the determination condition of Step S305 is not satisfied (Step S305: No), the measurement unit 41 determines whether or not the recovering rotational direction is not the CCW direction (Step S310). When the recovering rotational direction is not the CCW direction (Step S310: Yes), "1" is added to the shift count (Step S311), and the process is terminated.

In other words, as illustrated in FIG. 11, when "Step S304: Yes" and "Step S305: No" are satisfied, the rotational direction of the motor 11 is the CCW direction. When "Step S310: Yes" is satisfied, the recovering rotational direction is the CW direction, and thus "1" is added to the shift count.

When the determination condition of Step S310 is not satisfied (Step S310: No), in other words, when the rotational direction of the motor 11 is the CCW direction that is the same as the recovering rotational direction, the measurement unit 41 determines whether or not the shift count is larger than "0" (Step S312). Here, when the shift count is larger than "0" (Step S312: Yes), "1" is subtracted from the shift count (Step S313), and the process is terminated; otherwise (Step S312: No), the process is terminated without any change.

Furthermore, when the determination condition of Step S304 is not satisfied (Step S304: No), the measurement unit 41 determines whether or not the current value of the A-phase encoder signal equals to a value of the A-phase encoder signal in the previous process (Step S314).

Next, the current value of the A-phase encoder signal does not equal to the value of the A-phase encoder signal in the previous process (Step S314: Yes), the measurement unit 41 determines whether or not the recovering rotational direction is not the CW direction (Step S315). When the recovering rotational direction is not the CW direction (Step S315: Yes), "1" is added to the shift count (Step S316), and the process is terminated.

In other words, as illustrated in FIG. 11, when "Step S304: No" and "Step S314: Yes" are satisfied, the rotational direction of the motor 11 is the CW direction. When "Step S315: Yes" is satisfied, the recovering rotational direction is the CCW direction, and thus "1" is added to the shift count.

When the determination condition of Step S315 is not satisfied (Step S315: No), in other words, when the rotational direction of the motor 11 is the CW direction that is the same as the recovering rotational direction, the measurement unit 41 determines whether or not the shift count is larger than "0" (Step S317). Here, when the shift count is larger than "0" (Step S317: Yes), "1" is subtracted from the shift count (Step S318), and the process is terminated; otherwise (Step S317: No), the process is terminated without any change.

When the determination condition of Step S314 is not satisfied (Step S314: No), the measurement unit 41 determines whether or not the recovering rotational direction is not the CCW direction (Step S319). When the recovering rotational direction is not the CCW direction (Step S319: Yes), "1" is added to the shift count (Step S320), and the process is terminated.

In other words, as illustrated in FIG. 11, when "Step S304: No" and "Step S314: No" are satisfied, the rotational direction of the motor 11 is the CCW direction. When "Step S319: Yes" is satisfied, the recovering rotational direction is the CW direction, and "1" is added to the shift count.

When the determination condition of Step S319 is not satisfied (Step S319: No), in other words, when the rotational direction of the motor 11 is the CCW direction that is the same as the recovering rotational direction, the measurement unit 41 determines whether or not the shift count is larger than "0" (Step S321). Here, when the shift count is larger than "0" (Step S321: Yes), "1" is subtracted from the shift count (Step S322), and the process is terminated; otherwise (Step S321: No), the process is terminated without any change.

In this manner, the shift count is measured on the basis of an encoder signal that is output from the encoder 14 having a higher resolution than the hall element 15, so that it is possible to detect the shift of the motor 11 and its recovering rotational direction immediately after the rotational position of the motor 11 has been shifted.

Figure 16:
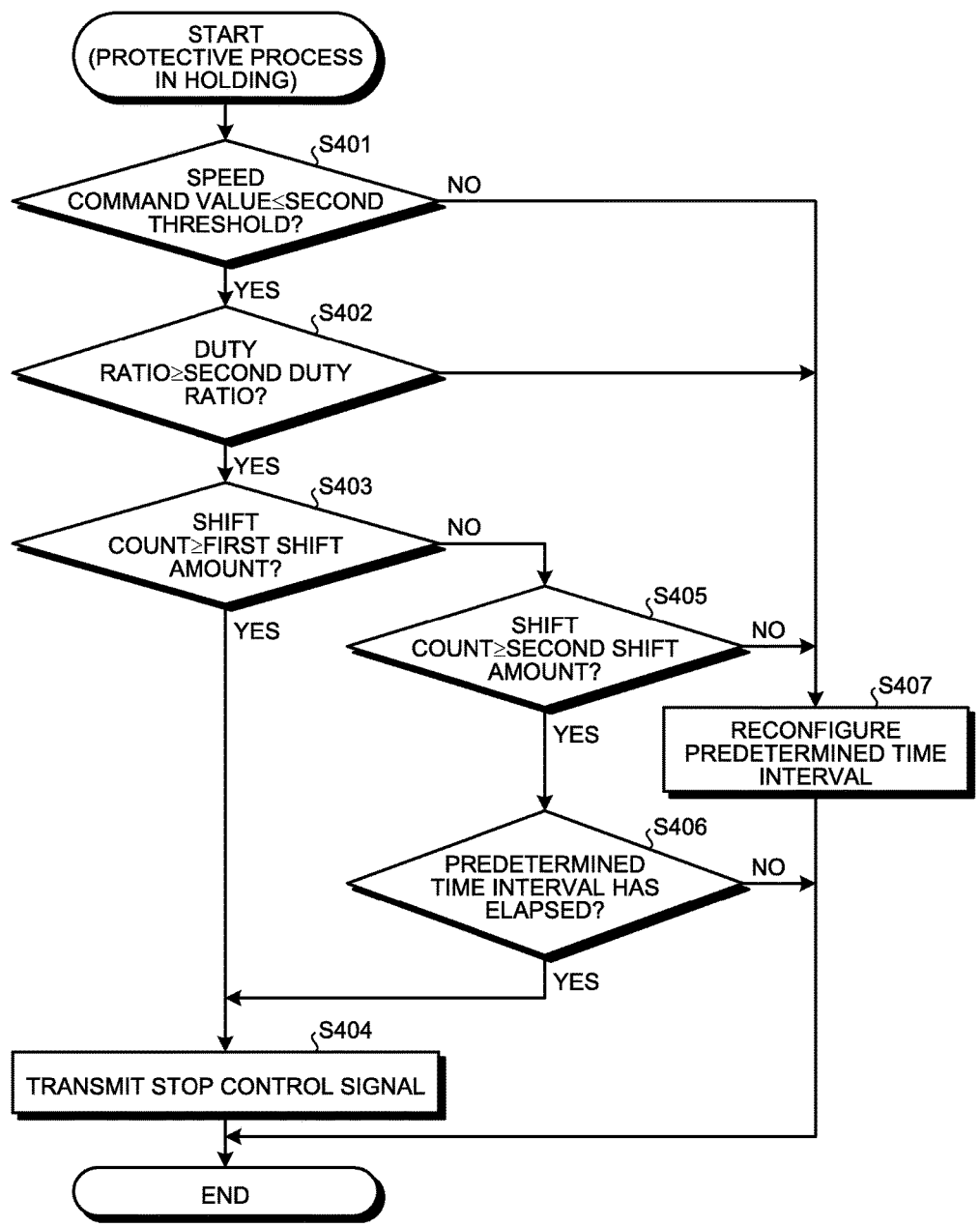
FIG. 16 is a flowchart illustrating a process for transmitting a stop control signal during motor holding period according to the embodiment.

FIG. 16 is a flowchart illustrating a process for transmitting the stop control signal during a motor holding period according to the embodiment. The process for transmitting the stop control signal illustrated in FIG. 16 is periodically performed. Note that this process is not performed during the protective operation performed by the motor driver 13.

As illustrated in FIG. 16, the transmitting unit 43 determines whether or not a speed command value commanded by the speed command signal is equal to or less than a predetermined second threshold that is smaller than the first threshold (Step S401). When the speed command value is the second threshold or less (Step S401: Yes), the transmitting unit 43 determines whether or not the duty ratio of the PWM signal is a predetermined second duty ratio or more (Step S402). This second duty ratio is another example of the duty ratio threshold stored in the duty-ratio threshold information 53, and is equal to or less than the first duty ratio in the above-mentioned transmitting process during the motor driving period.

Next, when the duty ratio of the PWM signal is the second duty ratio or more (Step S402: Yes), the transmitting unit 43 determines whether or not the shift count is equal to or more than a count value corresponding to a predetermined first shift amount (Step S403). This first shift amount is another example of the count threshold stored in the count threshold information 52.

When the determination condition of Step S401 is not satisfied (Step S401: No), or when that of Step S402 is not satisfied (Step S402: No), the transmitting unit 43 reconfigures a predetermined time interval (Step S407), and the process is terminated.

Next, when the shift count is the first shift amount or more (Step S403: Yes), the transmitting unit 43 transmits a stop control signal for stopping the motor 11 to the motor driver 13 (Step S404), and the process is terminated. Thus, the motor 11 is stopped.

When the determination condition of Step S403 is not satisfied (Step S403: No), the transmitting unit 43 determines whether or not the shift count is equal to or more than a count value corresponding to a predetermined second shift amount that is smaller than the first shift amount (Step S405). This second shift amount is another example of the count threshold stored in the count threshold information 52, and is a value smaller than the above-mentioned first shift amount.

Next, when the shift count is the second shift amount or more (Step S405: Yes), the transmitting unit 43 determines whether or not a predetermined time interval has elapsed (Step S406). When the predetermined time point has elapsed (Step S406: Yes), the transmitting unit 43 transmits a stop control signal for stopping the motor 11 to the motor driver 13 (Step S404), and the process is terminated. Thus, the motor 11 is stopped. When the predetermined time interval has not elapsed (Step S406: No), the process is terminated.

When the determination condition of Step S405 is not satisfied (Step S405: No), the transmitting unit 43 reconfigures the predetermined time interval (Step S407), and the process is terminated.

As described above, the transmitting unit 43 transmits the stop control signal to the motor driver 13 so as to stop the motor 11, when a shift amount from a target rotational position that is a stop position is the predetermined first shift amount or more and the duty ratio of the PWM signal is the second duty ratio or more, in a state where the rotational position of the motor 11 is being held. Thus, it is possible to suppress a rapid start of the motor 11, because the rapid start is caused by the re-drive in a state where the load is increased by an external factor from the stop position of the motor 11 during motor holding period, the rotational state of the motor 11 becomes different from that commanded by the commanded rotational state, and a force in accordance therewith for returning the rotational position of the motor 11 to the stop position is continued.

In a state where the rotational position of the motor 11 is being held, the second duty ratio that is used as a threshold for determination is set to a value less than the first duty ratio. The first duty ratio is a threshold while the motor 11 is being driven. In this manner, the threshold of the duty ratio is set to be different between during the motor holding period and during the motor driving period, so that it is possible to appropriately reduce the heat generation when the motor 11 generates more heat during the motor holding period than during the motor driving period, for example.

Furthermore, when the shift amount from the target rotational position that is a stop position becomes equal to or more than the predetermined second shift amount that is smaller than the first shift amount and the duty ratio of the PWM signal becomes the second duty ratio or more, in a state where the rotational position of the motor 11 is being held, the transmitting unit 43 transmits the stop control signal to the motor driver 13 after a predetermined time interval has elapsed. Thus, it is possible to suppress abnormal heating of the motor 11, which is caused by continuous application of the force for returning the rotational position of the motor 11 to the stop position during the motor holding period.

As described above, according to the present embodiment, the shift count is measured on the basis of the encoder signal transmitted from the encoder 14, and the stop control signal for stopping the motor 11 is transmitted from the motor driver 13 on the basis of this shift count and the duty ratio of the PWM signal. Thus, it is possible to safely control operations of the motor 11 in a rotational state that is not in conformity with a commanded rotational state due to an external factor.

In the above-mentioned embodiment, the case is exemplified in which the speed command signal generator 100 and the rotational direction signal generator 110 are external devices, at least one of the speed command signal generator 100 and the rotational direction signal generator 110 may be arranged inside of the motor apparatus 10 as the motor drive controlling apparatus.

In the above-mentioned embodiment, the case is exemplified in which the motor 11 is a brushless DC motor. However, the motor drive controlling method explained in the above-mentioned embodiment is able to be applied to a motor that is provided with a position detector (encoder 14) for outputting a pulse signal according to a clock signal and is able to control its rotational speed by using the clock signal.

In the above-mentioned embodiment, the blood pump 1 for delivering blood in the tubes 2 is explained to be one example of a tube pump. However, the motor drive controlling method explained in the above-mentioned embodiment may be applied to a tube pump for delivering physiological saline solution or any other liquid.

In the above-mentioned embodiment, the case is exemplified in which the encoder 14 is used as a position detector and the hall element 15 is used as a magnetic sensor. However, the position detector is not limited to the encoder, and the magnetic sensor is not limited to the hall element.

As described above, the motor drive controlling apparatus according to the embodiment includes: (i) the controller 12 that generates and outputs a drive control signal, in response to an input of a speed command signal and a rotational direction signal; (ii) the motor driver 13 that generates a drive signal and outputs the generated drive signal to the motor 11, in response to an input of the drive control signal; and (iii) a position detector (encoder 14) that detects a rotational position of the motor 11 and outputs a detection signal (encoder signal) that is based on this detection result. The controller 12 includes: (a) the measurement unit 41 that detects, on the basis of the detection signal (encoder signal), a time point at which a rotational state of the motor 11 becomes, caused by an external factor, a different state that is different from a commanded rotational state based on a combination of the speed command signal and the rotational direction signal, and measures a movement amount from a rotational position at the time point at which the rotational state of the motor 11 becomes the different state; and (b) the transmitting unit 43 that transmits, to the motor driver 13, a stop control signal for stopping an output of the drive signal, when the movement amount and an outputting state of the drive control signal satisfy a predetermined condition. Thus, it is possible to safely control operations of the motor 11 in a rotational state that is not in conformity with a commanded rotational state due to an external factor.

In the motor drive controlling apparatus according to the embodiment, the drive control signal includes a PWM signal, and the transmitting unit 43 transmits the stop control signal to the motor driver 13 when a duty ratio of the PWM signal is a predetermined ratio or more. Thus, it is possible to reliably detect that the pump system 30 is in a heavy load state.

In the motor drive controlling apparatus according to the embodiment, the measurement unit 41 detects, on the basis of the detection signal (encoder signal), a time point at which a rotation of the motor 11 is, caused by an external factor, switched into a reverse direction that is reverse to a target rotational direction while the speed command signal and the rotational direction signal are being input, and measures, as the movement amount, a movement amount of the motor 11 in the reverse direction from a rotational position of the motor 11 at the time point at which the rotation of the motor 11 is switched, on the basis of the detection signal (encoder signal); and the transmitting unit 43 transmits the stop control signal to the motor driver 13 when the movement amount is a predetermined first movement amount or more and the duty ratio of the PMW signal is a predetermined first duty ratio or more. Thus, it is possible to precisely detect a heavy load state so as to stop the motor 11.

In the motor drive controlling apparatus according to the embodiment, the transmitting unit 43 does not transmit the stop control signal to the motor driver 13, when the movement amount is the first movement amount or more and the duty ratio of the PMW signal does not exceed the first duty ratio, in a state where a current rotational position of the motor 11 based on the detection signal (encoder signal) precedes a target rotational position based on the speed command signal while the speed command signal and the rotational direction signal are being input. Thus, it is possible to continue to drive the motor 11 when the pump system 30 is not in a heavy load state.

In the motor drive controlling apparatus according to the embodiment, the transmitting unit 43 transmits the stop control signal to the motor driver 13, when the movement amount is equal to or more than a predetermined second movement amount that is the first movement amount or more, in a state where the current rotational position of the motor 11 precedes the target rotational position while the speed command signal and the rotational direction signal are being input, even when the duty ratio of the PMW signal does not exceed the first duty ratio. Thus, it is possible to stop the motor 11 when the feed amount of liquid largely fluctuates even in a state where the pump system 30 is not in a heavy load state.

In the motor drive controlling apparatus according to the embodiment, the measurement unit 41 detects, on the basis of the detection signal (encoder signal), a time point at which the motor 11 starts to be rotated due to an external factor in a state where the speed command signal is not input, and measures as the movement amount, on the basis of the detection signal (encoder signal), a shift amount from a rotational position of the motor 11 at the time point at which the motor 11 starts to be rotated, and the transmitting unit 43 transmits the stop control signal to the motor driver 13 when the shift amount is a predetermined first shift amount or more and the duty ratio of PMW signal is a predetermined second duty ratio or more. Even in a state where the rotational state of the motor 11 becomes, due to an external factor, not in conformity with the commanded rotational state from the stop position during torque holding, and a force for returning the rotational position of the motor 11 to the stop position is accordingly generated, it is possible to suppress a rapid start of the motor 11 caused by the drive from a state where the rotational position of the motor 11 is kept at the position.

In the motor drive controlling apparatus according to the embodiment, the second duty ratio of the PMW signal is the first duty ratio or less. Thus, it is possible to specify that the motor 11 is in a holding state so as to suppress the heat generation.

In the motor drive controlling apparatus according to the embodiment, when the shift amount becomes equal to or more than a predetermined second shift amount that is smaller than the first shift amount and the duty ratio of the PMW signal becomes the second duty ratio or more, in a state where the speed command signal is not input, the transmitting unit 43 transmits the stop control signal to the motor driver 13 after a predetermined time interval has elapsed. Thus, it is possible to suppress abnormal heating of the motor 11, which is caused by continuous application of the force for returning the rotational position of the motor 11 to the stop position during torque holding.

In the motor drive controlling apparatus according to the embodiment, the transmitting unit 43 does not transmit the stop control signal to the motor driver 13 when a rotational speed of the motor 11 set by the speed command signal is a predetermined threshold or more. Thus, it is possible to omit redundant determinations in the controller 12, thereby leading to increase in processing ability of the controller 12.

The tube pump according to the embodiment includes: the motor 11; the rollers 34*a* and 34*b* that are rotatably driven by the motor 11, and press the tube 2 to deliver liquid contained in the tube 2; and the motor drive controlling apparatus that performs the above-mentioned motor drive controlling method. Thus, it is possible to safely control operations of the motor 11 in a rotational state that is not in conformity with a commanded rotational state due to an external factor.

According to one aspect of the embodiment, it is possible to safely control operations of a motor in a rotational state that is not in conformity with a commanded rotational state due to an external factor.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A motor drive controlling apparatus comprising:
   a controller that generates and outputs a drive control signal, in response to an input of a speed command signal and a rotational direction signal;
   a motor driver that generates a drive signal and outputs the generated drive signal to a motor, in response to an input of the drive control signal; and
   a position detector that detects a rotational position of the motor and outputs a detection signal that is based on a detection result, wherein
   the controller includes:
      a measurement unit that detects, based on the detection signal, a time point at which a rotational state of the motor becomes, caused by an external factor, a different state that is different from a commanded rotational state based on a combination of the speed command signal and the rotational direction signal, and measures a movement amount from a rotational position at the time point at which the rotational state of the motor becomes the different state; and
      a transmitting unit that transmits, to the motor driver, a stop control signal for stopping an output of the drive signal, when the movement amount and an outputting state of the drive control signal satisfy a predetermined condition.

2. The motor drive controlling apparatus according to claim 1, wherein
   the drive control signal includes a pulse width modulation (PWM) signal, and
   the transmitting unit transmits the stop control signal to the motor driver when a duty ratio of the PWM signal is a predetermined ratio or more.

3. The motor drive controlling apparatus according to claim 2, wherein
   the measurement unit detects, based on the detection signal, a time point at which a rotation of the motor is, caused by an external factor, switched into a reverse direction that is reverse to a target rotational direction while the speed command signal and the rotational direction signal are being input, and measures, as the movement amount, a movement amount of the motor in the reverse direction from a rotational position of the motor at the time point at which the rotation of the motor is switched, based on the detection signal; and
   the transmitting unit transmits the stop control signal to the motor driver when the movement amount is a predetermined first movement amount or more and the duty ratio is a predetermined first duty ratio or more.

4. The motor drive controlling apparatus according to claim 3, wherein the transmitting unit does not transmit the stop control signal to the motor driver, when the movement amount is the first movement amount or more and the duty ratio does not exceed the first duty ratio, in a state where a current rotational position of the motor based on the detection signal precedes a target rotational position based on the speed command signal while the speed command signal and the rotational direction signal are being input.

5. The motor drive controlling apparatus according to claim 4, wherein the transmitting unit transmits the stop control signal to the motor driver, when the movement amount is equal to or more than a predetermined second movement amount that is the first movement amount or more, in a state where the current rotational position of the motor precedes the target rotational position while the speed command signal and the rotational direction signal are being input, even when the duty ratio does not exceed the first duty ratio.

6. The motor drive controlling apparatus according to claim 3, wherein
   the measurement unit detects, based on the detection signal, a time point at which the motor starts to be rotated due to an external factor in a state where the speed command signal is not input, and measures as the movement amount, based on the detection signal, a shift amount from a rotational position of the motor at the time point at which the motor starts to be rotated, and
   the transmitting unit transmits the stop control signal to the motor driver when the shift amount is a predetermined first shift amount or more and the duty ratio is a predetermined second duty ratio or more.

7. The motor drive controlling apparatus according to claim 6, wherein the second duty ratio is equal to or less than the first duty ratio.

8. The motor drive controlling apparatus according to claim 6, wherein when the shift amount becomes equal to or more than a predetermined second shift amount that is smaller than the first shift amount and the duty ratio becomes equal to or more than the second duty ratio, in a state where the speed command signal is not input, the transmitting unit transmits the stop control signal to the motor driver after a predetermined time interval has elapsed.

9. The motor drive controlling apparatus according to claim 1, wherein the transmitting unit does not transmit the stop control signal to the motor driver when a rotational speed of the motor set by the speed command signal is a predetermined threshold or more.

10. A motor drive controlling method that is performed by a controller, the method comprising:
    detecting, based on a detection signal output from a position detector that detects a rotational position of a motor, a time point at which a rotational state of the motor becomes, caused by an external factor, a different state that is different from a commanded rotational state based on a combination of a speed command signal and a rotational direction signal, and measuring a movement amount from a rotational position at the time point at which the rotational state of the motor becomes the different state; and
    transmitting, to a motor driver, a stop control signal for stopping an output of a drive signal, when the movement amount and an outputting state of a drive control signal satisfy a predetermined condition, the drive control signal being generated by the controller.

11. A tube pump comprising:
    a motor;

one or more rollers that are rotated by drive of the motor, and press a tube to deliver liquid contained in the tube;

a motor drive controlling apparatus including:
- a controller that generates and outputs a drive control signal, in response to an input of a speed command signal and a rotational direction signal;
- a motor driver that generates a drive signal and outputs the generated drive signal to a motor, in response to an input of the drive control signal; and
- a position detector that detects a rotational position of the motor and outputs a detection signal that is based on a detection result, wherein the controller includes:
- a measurement unit that detects, based on the detection signal, a time point at which a rotational state of the motor becomes, caused by an external factor, a different state that is different from a commanded rotational state based on a combination of the speed command signal and the rotational direction signal, and measures a movement amount from a rotational position at the time point at which the rotational state of the motor becomes the different state; and
- a transmitting unit that transmits, to the motor driver, a stop control signal for stopping an output of the drive signal, when the movement amount and an outputting state of the drive control signal satisfy a predetermined condition.

* * * * *